United States Patent
Komiyama et al.

(10) Patent No.: US 10,189,847 B2
(45) Date of Patent: Jan. 29, 2019

(54) OXIME ESTER COMPOUND AND PHOTOPOLYMERIZATION INITIATOR CONTAINING SAID COMPOUND

(71) Applicant: ADEKA CORPORATION, Tokyo (JP)

(72) Inventors: Yoko Komiyama, Tokyo (JP); Takeo Oishi, Tokyo (JP); Tomoyuki Ariyoshi, Tokyo (JP); Tomoya Tamachi, Tokyo (JP); Takayuki Ikaga, Tokyo (JP); Naomi Sato, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/129,630

(22) PCT Filed: Mar. 30, 2015

(86) PCT No.: PCT/JP2015/059928
§ 371 (c)(1),
(2) Date: Sep. 27, 2016

(87) PCT Pub. No.: WO2015/152153
PCT Pub. Date: Oct. 8, 2015

(65) Prior Publication Data
US 2017/0166575 A1 Jun. 15, 2017

(30) Foreign Application Priority Data
Apr. 4, 2014 (JP) ................ 2014-078080

(51) Int. Cl.
| | | |
|---|---|---|
| *C07D 243/36* | (2006.01) | |
| *G03F 7/004* | (2006.01) | |
| *C07D 487/06* | (2006.01) | |
| *C07D 209/14* | (2006.01) | |
| *C08F 2/50* | (2006.01) | |
| *G03F 7/027* | (2006.01) | |
| *G03F 7/031* | (2006.01) | |
| *C07D 401/04* | (2006.01) | |
| *C07D 405/04* | (2006.01) | |
| *C07D 409/04* | (2006.01) | |
| *C07D 209/56* | (2006.01) | |
| *C07D 209/60* | (2006.01) | |

(Continued)

(52) U.S. Cl.
CPC ......... *C07D 487/06* (2013.01); *C07D 209/14* (2013.01); *C07D 209/56* (2013.01); *C07D 209/60* (2013.01); *C07D 401/04* (2013.01); *C07D 405/04* (2013.01); *C07D 409/04* (2013.01); *C07D 409/10* (2013.01); *C07D 471/04* (2013.01); *C08F 2/50* (2013.01); *G03F 7/004* (2013.01); *G03F 7/027* (2013.01); *G03F 7/031* (2013.01)

(58) Field of Classification Search
CPC ........... C07D 209/14; C07D 209/209; C07D 209/56; C07D 209/60; C07D 401/04; C07D 405/04; C07D 409/04; C07D 409/10; C07D 471/04; C08D 2/50; G03F 7/0007; G03F 7/0004; G03F 7/027; G03F 7/031
USPC ................................. 430/7, 281.1
See application file for complete search history.

(56) References Cited

U.S. PATENT DOCUMENTS

| | | |
|---|---|---|
| 5,866,594 A | 2/1999 | Endo |
| 6,596,445 B1 | 7/2003 | Matsumoto et al. |
| 7,648,738 B2 | 1/2010 | Tanabe et al. |

(Continued)

FOREIGN PATENT DOCUMENTS

| | | |
|---|---|---|
| CN | 101747254 | 6/2010 |
| DE | 2707268 A1 | 8/1978 |

(Continued)

OTHER PUBLICATIONS

Computer-generated translation of WO 2013/008652 (Jan. 2013).*
Computer-generated translation of FR 2244499 (Apr. 1975).*
International Search Report, PCT/JP2015/059928, dated Jun. 23, 2015.
Alonso et al., "Photochemistry of acyloximes: synthesis of heterocycles and natural products", Tetrahedron, 2010, 66(46), 8828-8831, Scheme3.
Enders D et al., "N-Hetrocyclic carbene catalyzed synthesis of oxime esterst", Organic & Biomolecular Chemistry, 2013, 11(1), 138-141, Table2 Entry12.
Extended European Search Report dated Oct. 6, 2017; Application No. 15773324.7.

(Continued)

*Primary Examiner* — John A McPherson
(74) *Attorney, Agent, or Firm* — Young & Thompson

(57) ABSTRACT
An oxime ester compound represented by general formula (I), wherein $R^1$ to $R^8$ are as defined in the description, and n is 0 or 1; a photopolymerization initiator containing the compound; a photosensitive composition, alkali-developable photosensitive resin composition, and colored alkali-developable photosensitive resin composition containing the photopolymerization initiator; and a cured product of these compositions are provided. The compound is useful as a high-sensitivity photopolymerization initiator that has good stability and low sublimability and that efficiently absorbs, and is activated by, near-ultraviolet light, e.g., at 365 nm.

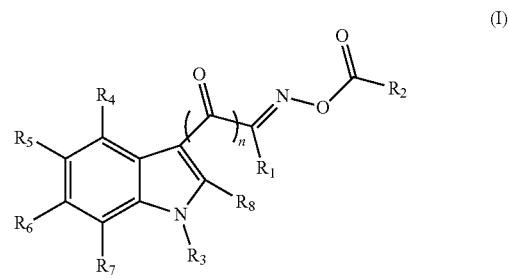

16 Claims, No Drawings

(51) Int. Cl.
*C07D 409/10* (2006.01)
*C07D 471/04* (2006.01)

(56) References Cited

U.S. PATENT DOCUMENTS

| | | | |
|---|---|---|---|
| 2002/0020832 A1* | 2/2002 | Oka | C08F 2/50 252/500 |
| 2006/0241259 A1 | 10/2006 | Tanabe et al. | |
| 2007/0037785 A1 | 2/2007 | Ansorge | |
| 2008/0146745 A1 | 6/2008 | Luo et al. | |
| 2009/0163545 A1 | 6/2009 | Goldfarb | |

FOREIGN PATENT DOCUMENTS

| | | |
|---|---|---|
| EP | 0791582 A1 | 8/1997 |
| FR | 2244499 | 4/1975 |
| FR | 2244501 A1 | 4/1975 |
| JP | 2006-516246 | 6/2006 |
| JP | 2007-219362 | 8/2007 |
| WO | 2005037779 A2 | 4/2005 |
| WO | WO 2013/008652 | 1/2013 |

OTHER PUBLICATIONS

Mamaev et al: "Amino Acids of the Indole Series, III, gamma-amino-gamma-(3-indolyl)butyric acid", Izvestiya Sibirskogo Otdeleniya Akademii Nauk SSSR, Seriya Khimicheskikh Nauk, vol. 3., Nov. 1, 1963 (Nov. 1, 1963); pp. 97-102, XP9500300.
Pedras & Yaya et al: "ESI Electronic Supplementary Information for Dissecting metabolic puzzles through isotope feeding: a novel amino acid in the biosynthetic pathway of cruciferous phytoalexins rapalexin A and isocyalexin A", Dec. 14, 2012 (Dec. 14, 2012) XP55408565.
Qifan Wu et al.: :Divergent Syntheses of 2-Aminonicotinonitrelles ABD Pyrazolines by Copper-catalyzed Cyclization of Oxime Ester, Organic Letters, 14(23), 6012-6015 Coden: ORLEF7; ISSN: 1523-7052, vol. 16, No. 5, Mar. 7, 2014 (Mar. 7, 2014), pp. 1350-1353, XP55408582, ISSN: 1523-7060, DOI: 10.1021/pl50094w.
Kochhar MM et al.: "Synthesis of Ketoximino Esters as Potential Ataraxics". Journal of Pharmaceutical Sciences, American Chemical Society and American Pharmaceutical Association, vol. 54, No. 8, Aug. 1, 1965 (Aug. 1, 1965), pp. 1149-1152, XP009500299, ISSN: 0022-3549, DOI: 10.1002/JPS.2600540811.
Gao et al.: "Synthesis of Novel 1-alkyl-2-chloro(alkoxy)-1H-indole 3-carbaldehyde oximes and oxime-ethers (esters) derivatives", Chemical Research in Chinese Universities, vol. 25, No. 4, Jan. 1, 2009 (Jan. 1, 2009), pp. 465-473, XP9500303, Scheme 4; compounds 10a-d, 11a-d.
Ernest Wenkert et al: "3-Hydroxymethyleneoxindole and its Derivatives", Journal of the American Chemical Society, vol. 81, No. 14, Jul. 1, 1959 (Jul. 1, 1959), pp. 3763-3768, XP55408933, US ISSN: 0002-7863, DOI: 10.1021/ja01523a068 *compound XIJ*.
Shuai Wang et al: "A Direct Copper-Promoted Three-Component Entry to Trifluromethylketoximes", Organic Letters, 14(23), 6012-6015 Coden: ORLEF7; ISSN: 1523-7052, vol. 16, No. 6, Mar. 21, 2014 (Mar. 21, 2014), pp. 1606-1609, XP55408930, ISSN: 1523-7060, DOI: 10.1021/01500203m * Scheme 2; compound 6 *.
Database CA [Online] Chemical Abstracts Service, Columbus, Ohio, US; Misztal, Stanislaw et al: "Synthesis and pharmacologic properties of pyridoyl derivatives of 3-methylaminoindole 2-methyltrptamie and isotryptamine", XP002774023, retrieved from STN Database accession No. 1977:439214 * abstract *, (1977).
STN Columbus, Copyright 2018 American Chemical Society (ACS).

* cited by examiner

OXIME ESTER COMPOUND AND PHOTOPOLYMERIZATION INITIATOR CONTAINING SAID COMPOUND

TECHNICAL FIELD

This invention relates to a novel oxime ester compound useful as a photopolymerization initiator in a photosensitive composition, a photopolymerization initiator containing the compound, and a photosensitive composition containing a polymerizable compound having an ethylenically unsaturated bond and the photopolymerization initiator.

BACKGROUND ART

A photosensitive composition contains a polymerizable compound having an ethylenically unsaturated bond and a photopolymerization initiator. A photosensitive composition polymerizes to cure on being irradiated with energy rays (light) and is used in photo-curing inks, photosensitive printing plate precursors, various photoresists, and the like.

Patent documents 1 to 3 listed below propose using an oxime ester compound as a photopolymerization initiator of a photosensitive composition. However, the oxime ester compounds disclosed do not have satisfactory sensitivity.

A colored alkali-developable photosensitive resin composition containing a colorant for use as, for example, color filters is required to have high sensitivity. Therefore, a photoresist should have a high concentration of a photopolymerization initiator. However, a photopolymerization initiator of high concentration has raised problems, such as poor developability that causes scum or undeveloped residue formation and contamination of a photomask or a heating oven by sublimate.

CITATION LIST

Patent Document

Patent document 1: US6596445B1
Patent document 2: US2006241259A1
Patent document 3: WO 2013/008652

SUMMARY OF INVENTION

Technical Problem

The problem to be solved is that there has been no photopolymerization initiator having satisfactory sensitivity.

Accordingly, an object of the invention is to provide a novel compound useful as a high-sensitivity photopolymerization initiator that has good stability and low sublimability, and that efficiently absorbs, and is activated by, near-ultraviolet light, e.g., at 365 nm; a photopolymerization initiator containing the compound; and a photosensitive composition containing the compound.

Solution To Problem

The invention has accomplished the above object by providing a novel oxime ester compound represented by general formula (I) shown below and a photopolymerization initiator containing the compound.

[Chem. 1]

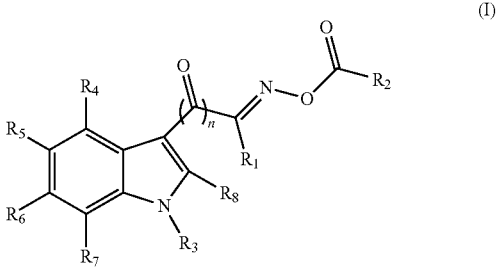

wherein $R^1$ and $R^2$ each independently represent $R^{11}$, $OR^{11}$, $COR^{11}$, $SR^{11}$, $CONR^{12}R^{13}$, or CN;

$R^{11}$, $R^{12}$, and $R^{13}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the hydrogen atom of the group represented by $R^{11}$, $R^{12}$, and $R^{13}$ being optionally replaced by $R^{21}$, $OR^{21}$, $COR^{21}$, $SR^{21}$, $NR^{22}R^{23}$, $CONR^{22}R^{23}$, —$NR^{22}$—$OR^{23}$, —$NCOR^{22}$—$OCOR^{23}$, $NR^{22}COR^{21}$, $OCOR21$, $COOR^{21}$, $SCOR^{21}$, $OCSR^{21}$, $COSR^{21}$, $CSOR^{21}$, a hydroxyl group, a nitro group, CN, a halogen atom, or $COOR^{21}$;

$R^{21}$, $R^{22}$, and $R^{23}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the hydrogen atom of the group represented by $R^{21}$, $R^{22}$, and $R^{23}$ being optionally replaced by a hydroxyl group, a nitro group, CN, a halogen atom, a hydroxyl group, or a carboxyl group, the alkylene moiety of the group represented by $R^{11}$, $R^{12}$, $R^{13}$, $R^{21}$, $R^{22}$, and $R^{23}$ being optionally interrupted by —O—, —S—, —COO—, —OCO—, —$NR^{24}$—, —$NR^{24}CO$—, —$NR^{24}COO$—, —$OCONR^{24}$—, —SCO—, —COS—, —OCS—, or —CSO— at 1 to 5 sites provided that no two oxygen atoms are directly bonded to each other;

$R^{24}$ represents a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the alkyl moiety of the group represented by $R^{11}$, $R^{12}$, $R^{13}$, $R^{21}$, $R^{22}$, $R^{23}$, and $R^{24}$ being optionally branched or cyclic;

$R^3$ represents a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the alkyl moiety of the group represented by $R^3$ being optionally branched or cyclic, $R^3$ and $R^7$, $R^3$ and $R^8$, $R^4$ and $R^5$, $R^5$ and $R^6$, and $R^6$ and $R^7$ being optionally taken together to form a ring, the hydrogen atom of the group represented by $R^3$ being optionally replaced by $R^{21}$, $OR^{21}$, $COR^{21}$, $SR^{21}$, $NR^{22}R^{23}$, $CONR^{22}R^{23}$, —$NR^{22}$—$OR^{23}$, —$NCOR^{22}$—$OCOR^{23}$, $NR^{22}COR^{21}$, $OCOR^{21}$ $COOR^{21}$, $SCOR^{21}$, $OCSR^{21}$, $COSR^{21}$, $CSOR^{21}$, a hydroxyl group, a nitro group, CN, a halogen atom, or $COOR^{21}$;

$R^4$, $R^5$, $R^6$, and $R^7$ each independently represent $R^{11}$, $OR^{11}$, $SR^{11}$, $COR^{14}$, $CONR^{15}R^{16}$, $NR^{12}COR^{11}$, $OCOR^{11}$, COOR$^{14}$, SCOR$^{11}$, OCSR$^{11}$, COSR$^{14}$, CSOR$^{11}$, a hydroxyl group, CN, or a halogen atom, R$^4$ and R$^5$, R$^5$ and R$^6$, and R$^6$ and R$^7$ being optionally taken together to form a ring;

R$^{14}$, R$^{15}$, and R$^{16}$ each represent a hydrogen atom or an alkyl group having 1 to 20 carbon atoms, the alkyl moiety of the group represented by R$^{R14}$, R$^{15}$, and R$^{16}$ being optionally branched or cyclic;

R$^8$ represents R$^{11}$, OR$^{11}$, SR$^{11}$, COR$^{11}$, CONR$^{12}$R$^{13}$, NR$^{12}$COR$^{11}$, OCOR$^{11}$, COOR$^{11}$, SCOR$^{11}$, OCSR$^{11}$, COSR$^{11}$, CSOR$^{11}$, a hydroxyl group, CN, or a halogen atom; and n represents 0 or 1.

The invention also provides a photosensitive composition containing the photopolymerization initiator and a polymerizable compound having an ethylenically unsaturated bond.

The invention also provides an alkali-developable photosensitive resin composition containing the photosensitive composition and a compound having alkali developability and optionally having an ethylenically unsaturated group.

The invention also provides a colored alkali-developable photosensitive resin composition containing the alkali-developable photosensitive resin composition and a colorant.

The invention also provides a cured product obtained by irradiating the above-described photosensitive composition, alkali-developable photosensitive resin composition, or colored alkali-developable photosensitive resin composition with energy rays.

Effect of Invention

The oxime ester compound of the invention has good stability in the visible region and low sublimability, efficiently produces radicals on irradiation with emission lines, e.g., at 365 nm (i-lines), and is useful as a photopolymerization initiator in a photosensitive composition.

DESCRIPTION OF EMBODIMENTS

The oxime ester compound of the invention and the photopolymerizable initiator containing the compound will be described in detail with reference to their preferred embodiments.

The oxime ester compound of the invention is a novel compound represented by formula (I) shown above. The oxime ester compound embraces geometric isomers based on the double bond of oxime. Either of the isomers is useful with no distinction. While formula (I) representing the compounds of the invention, formula (II) (shown later) representing a preferred group of the compounds of formula (I), and the chemical structural formulae (shown later) of illustrative examples of the compounds each represent either one of the geometric isomers, the oxime ester compounds of the invention are not limited to those represented by these formulae and may be the other isomer or a mixture of the two isomers.

Examples of the C1-20 alkyl group as represented by R$^3$, R$^{11}$, R$^{12}$, R$^{13}$, R$^{14}$, R$^{15}$, R$^{16}$, R$^{21}$, R$^{22}$, R$^{23}$, and R$^{24}$ in formula (I) include methyl, ethyl, propyl, isopropyl, butyl, isobutyl, s-butyl, t-butyl, amyl, isoamyl, t-amyl, hexyl, heptyl, octyl, isooctyl, 2-ethylhexyl, t-octyl, nonyl, isononyl, decyl, isodecyl, undecyl, dodecyl, tetradecyl, hexadecyl, octadecyl, eicosyl, cyclopentyl, cyclopentylmethyl, cyclopentylethyl, cyclohexyl, cyclohexylmethyl, and cyclohexylethyl.

Examples of the C6-30 aryl group as represented by R$^3$, R$^{11}$, R$^{12}$, R$^{13}$, R$^{21}$, R$^{22}$, R$^{23}$, and R$^{24}$ include phenyl, tolyl, xylyl, ethylphenyl, naphthyl, anthryl, phenanthryl; and phenyl, biphenylyl, naphthyl or anthryl substituted with at least one of the above recited alkyl groups.

Examples of the C7-30 arylalkyl group as represented by R$^3$, R$^{11}$, R$^{12}$, R$^{13}$, R$^{21}$, R$^{22}$, R$^{23}$, and R$^{24}$ formula (I) include benzyl, α-methylbenzyl, α,α-dimethylbenzyl, and phenylethyl.

Examples of the C2-C20 heterocyclic group as represented by R$^3$, R$^{11}$, R$^{12}$, R$^{13}$, R$^{21}$, R$^{22}$, R$^{23}$, and R$^{24}$ in formula (I) include 5-to 7-membered heterocyclic groups, such as pyridyl, pyrimidyl, furyl, thienyl, tetrahydrofuryl, dioxolanyl, benzoxazol-2-yl, tetrahydropyranyl, pyrrolidyl, imidazolidyl, pyrazolidyl, thiazolidyl, isothiazolidyl, oxazolidyl, isooxazolidyl, piperidyl, piperazyl, and morpholinyl.

The ring formed by connecting R$^4$ and R$^5$; R$^5$ and R$^6$; R$^6$ and R$^7$; R$^3$ and R$^7$; or R$^3$ and R$^8$ is preferably a 5-to 7-membered ring, including cyclopentane, cyclohexane, cyclopentene, benzene, piperidine, morpholine, lactone, and lactam rings.

Examples of the halogen atom as represented by R$^4$, R$^5$, R$^6$, R$^7$, or R$^8$ in formula (I) and the halogen atom as a substituent of R$^3$, R$^{11}$, R$^{12}$, R$^{13}$, R$^{21}$, R$^{22}$, and R$^{23}$ in formula (I) include fluorine, chlorine, bromine, and iodine.

The alkylene moiety of the groups as represented by R$^{11}$, R$^{12}$, R$^{13}$, R$^{21}$, R$^{22}$, and R$^{23}$ in formula (I) may be interrupted by —O—, —S—, —COO—, —OCO—, —NR$^{24}$—, —NR$^{24}$CO—, —NR$^{24}$COO—, —OCONR$^{24}$—, —SCO—, —COS—, —OCS—, or —CSO— at 1 to 5 sites provided that no two oxygen atoms are directly bonded to each other. The interrupting groups may be the same or different. Two or more interrupting groups may be continued to each other, if possible.

The alkyl (alkylene) moiety of the groups represented by R$^{11}$, R$^{12}$, R$^{13}$, R$^{21}$, R$^{22}$, R$^{23}$, and R$^{24}$ in formula (I) may be branched or cyclic.

Preferred of the oxime ester compounds of the invention are those in which R$^3$ is an aromatic, optionally fused ring and compounds represented by general formula (II) shown below because of their high sensitivity and ease of synthesis.

[Chem. 2]

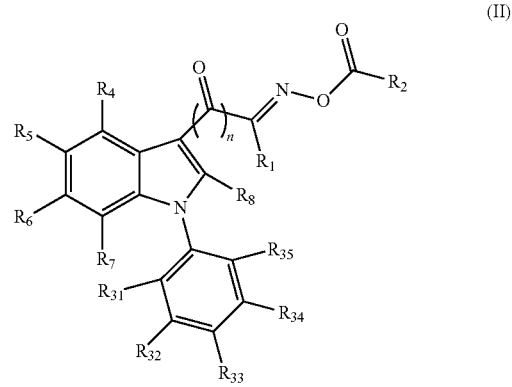

(II)

wherein R$^1$, R$^2$, R$^4$, R$^5$, R$^6$, R$^7$, R$^8$, and n are as defined for general formula (I); R$^{31}$, R$^{32}$, R$^{33}$, R$^{34}$, and R$^{35}$ each independently represent R$^{11}$, OR$^{11}$, COR$^{11}$, CONR$^{15}$R$^{16}$, NR$^2$COR$^{11}$, OCOR$^{11}$, COOR$^{14}$, SCOR$^{11}$, OCSR$^{11}$, COSR$^{14}$, CSOR$^{11}$, hydroxyl, nitro, CN, or halogen; R$^{31}$ and R$^{32}$, R$^{32}$ and R$^{33}$, R$^{33}$ and R$^{34}$, and R$^{34}$ and R$^{35}$ may be taken together to form a ring.

Examples of the ring formed by connecting $R^{31}$ and $R^{32}$, $R^{32}$ and $R^{33}$, $R^{33}$ and $R^{34}$, or $R^{34}$ and $R^{35}$ are the same as those described for the rings formed by connecting $R^4$ and $R^5$, $R^5$ and $R^6$, $R^6$ and $R^7$, $R^3$ and $R^7$, or $R^3$ and $R^8$.

Of the compounds having formulae (I) and (II) preferred are those in which $R^1$ is C1-C12 alkyl or C7-C15 arylalkyl, and is C6-C12 aryl or C1-C8 alkyl because of their high solvent solubility; those in which $R^2$ is methyl, ethyl, or phenyl because of their high reactivity; those in which $R^4$, $R^5$, $R^6$, and $R^7$ are each hydrogen or cyano, particularly hydrogen, because of ease of synthesis; those in which $R^8$ is hydrogen for ease of synthesis; and those in which n is 1 because of high sensitivity. Of the compounds having formula (II), those in which at least one of $R^{31}$, $R^{32}$, $R^{33}$, $R^{34}$, and $R^{35}$ is nitro, CN, halogen, or $COR^{11}$, and $R^{11}$ is C6-C12 aryl or C1-C8 alkyl because of high sensitivity are preferred; those in which at least one of $R^{31}$, $R^{32}$, $R^{33}$, $R^{34}$, and $R^{35}$ is nitro, CN, or halogen are more preferred; and those in which $R^{33}$ is nitro, CN, or halogen are even more preferred.

Accordingly, examples of preferred oxime ester compounds having formula (I) include, but are not limited to, compound Nos. 1 through 212 below.

[Chem. 3]

Compound No. 1

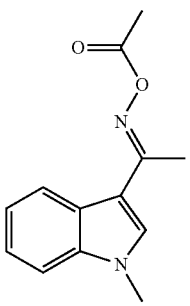

Compound No. 2

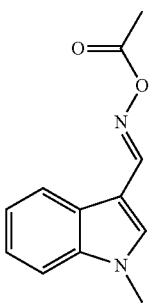

Compound No. 3

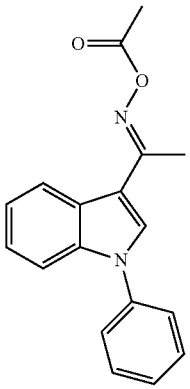

Compound No. 4

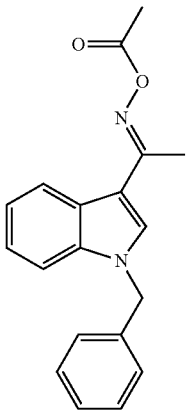

Compound No. 5

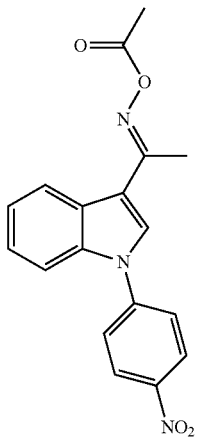

Compound No. 6

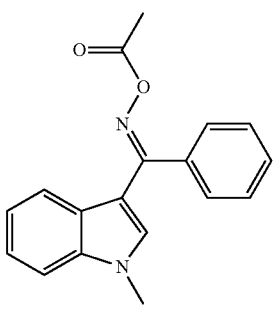

Compound No. 7

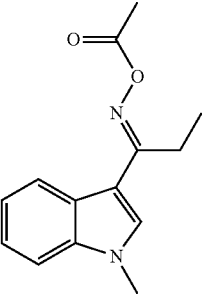

Compound No. 8
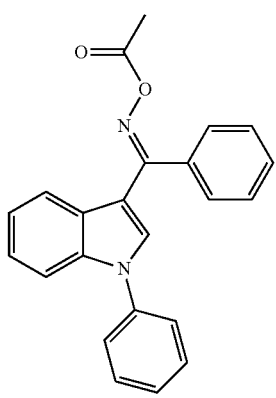
Compound No. 11
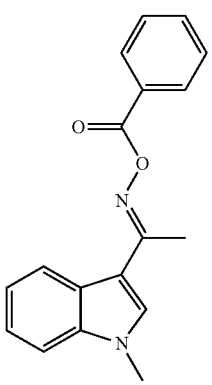
Compound No. 9
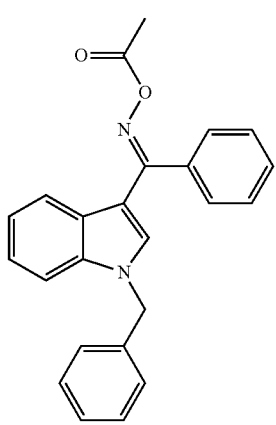
Compound No. 12
Compound No. 10
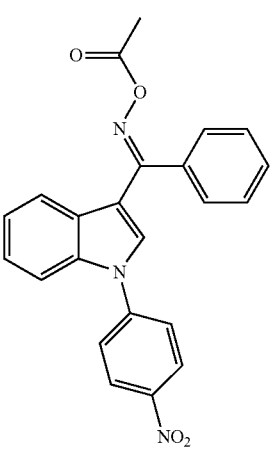
Compound No. 13
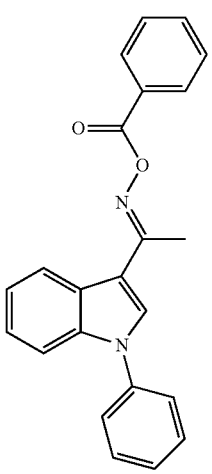

Compound No. 14
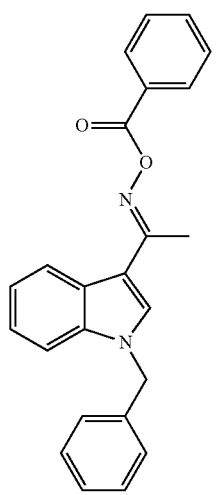
Compound No. 15
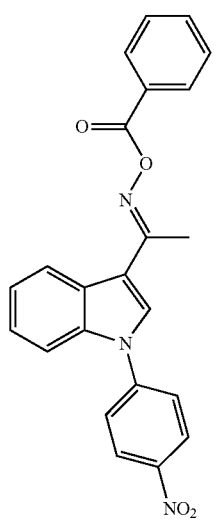
Compound No. 16
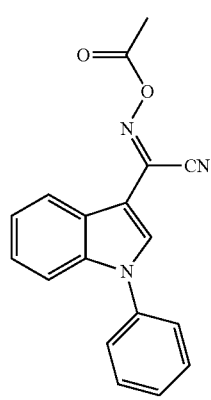
Compound No. 17
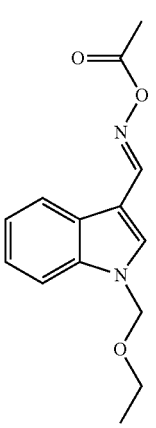
Compound No. 18
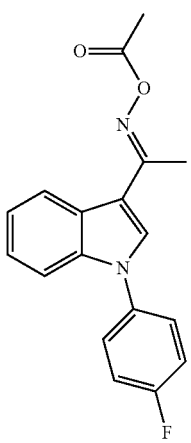
Compound No. 19
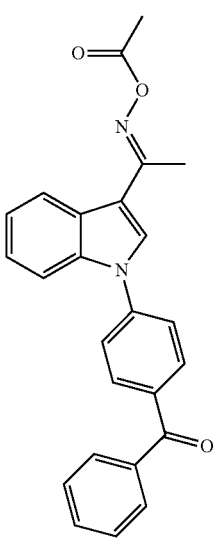

Compound No. 20
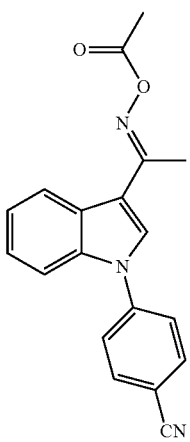
[Chem. 4]
Compound No. 21
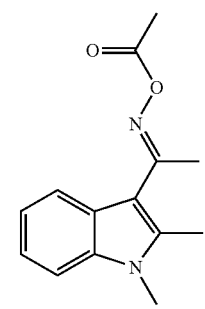
Compound No. 22
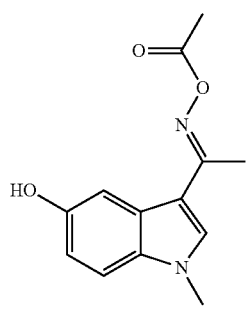
Compound No. 23
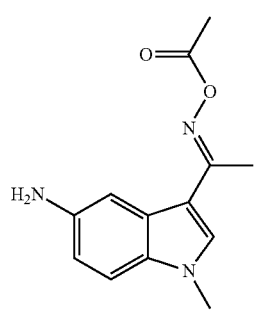
Compound No. 24
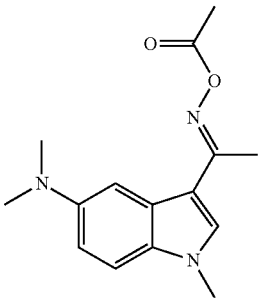
Compound No. 25
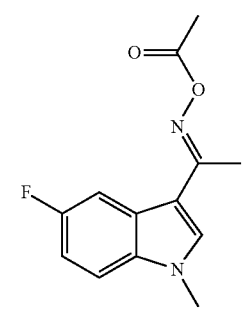
Compound No. 26
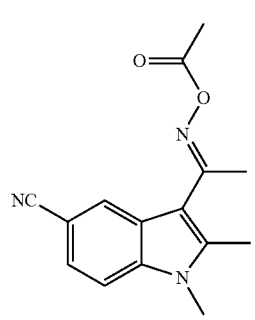
Compound No. 27
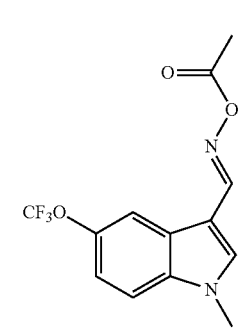
Compound No. 28
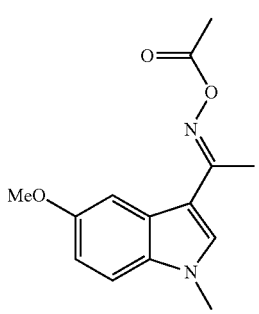

Compound No. 29
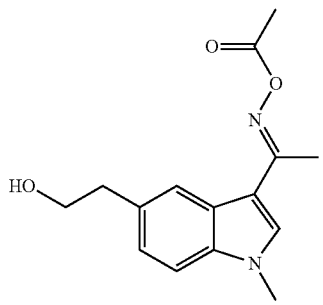
Compound No. 30
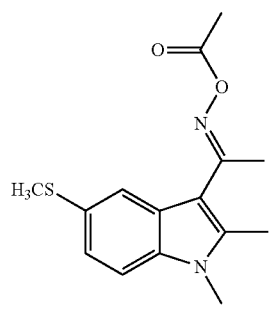
Compound No. 31
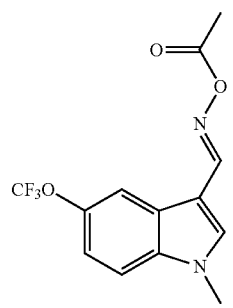
Compound No. 32
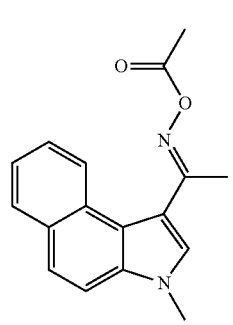
Compound No. 33
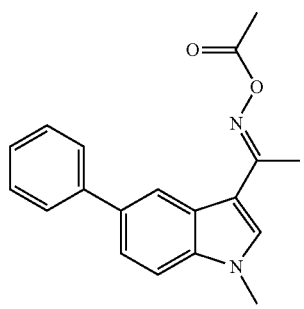
Compound No. 34
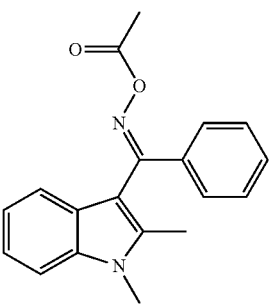
Compound No. 35
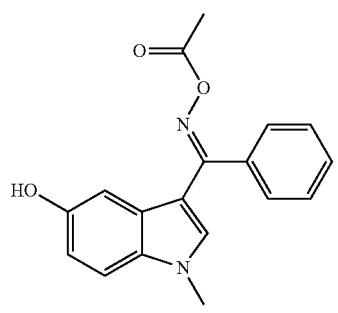
Compound No. 36
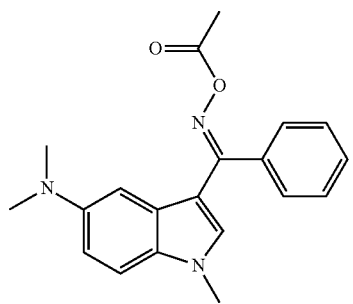
Compound No. 37
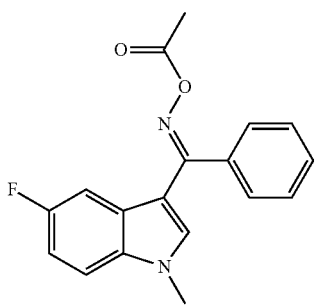

Compound No. 38
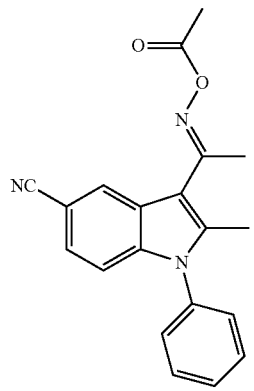
Compound No. 42
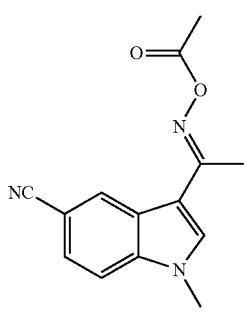
Compound No. 39
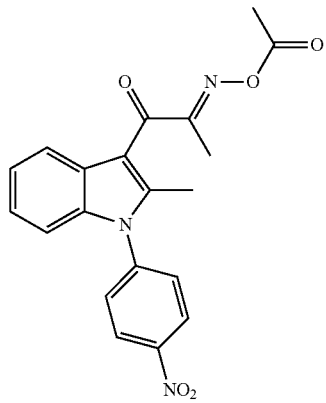
Compound No. 43
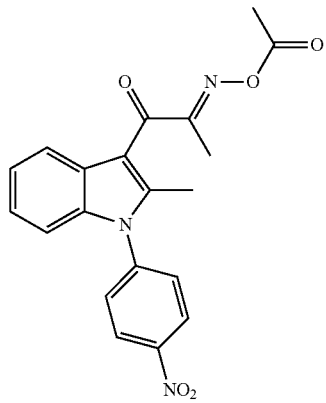
Compound No. 40
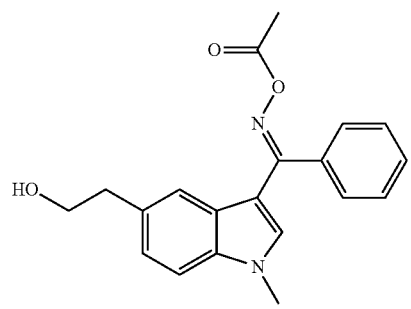
Compound No. 44
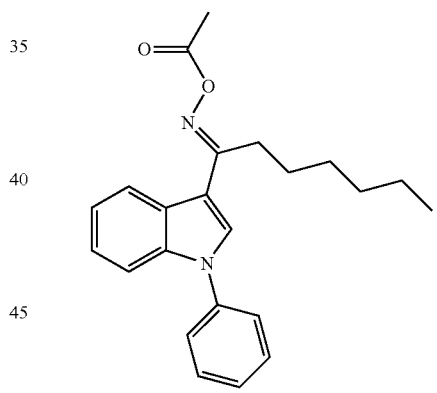
Compound No. 41
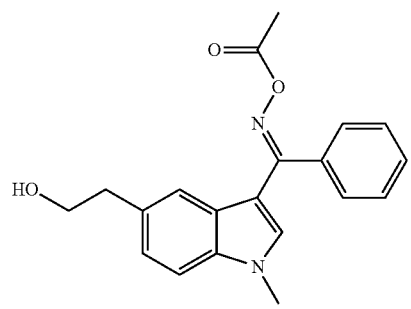
Compound No. 45
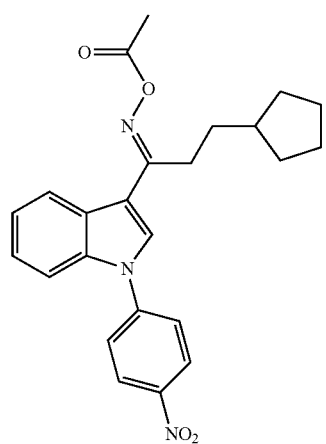

-continued
Compound No. 46
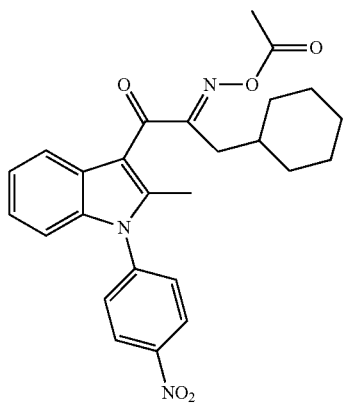
Compound No. 47
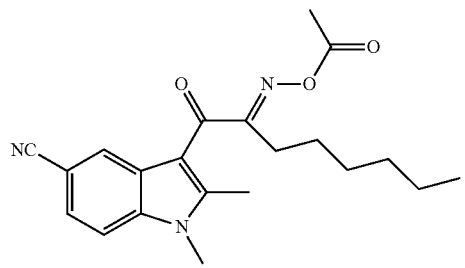
Compound No. 48
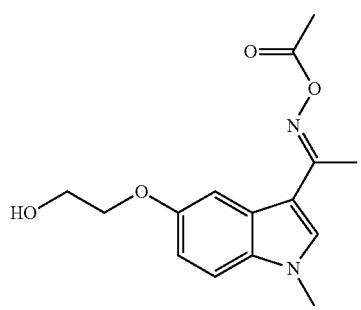
Compound No. 49
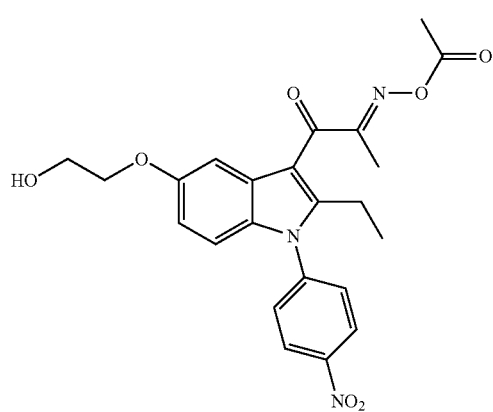
-continued
Compound No. 50
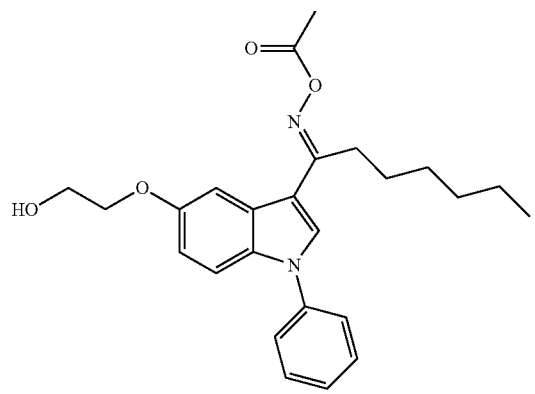
Compound No. 51
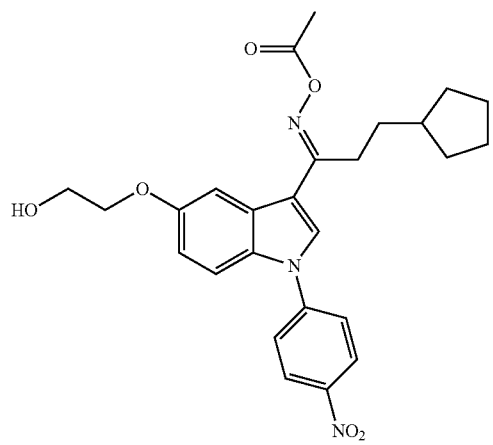
Compound No. 52
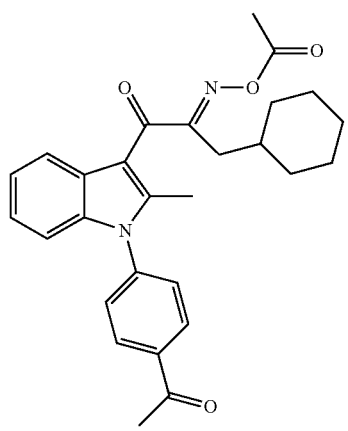

Compound No. 53
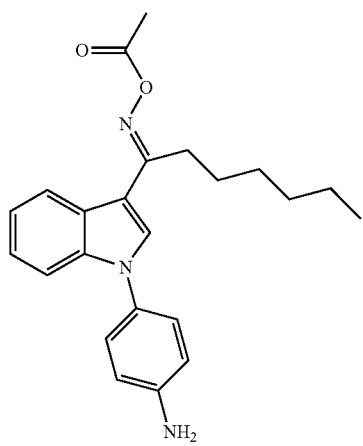
[Chem. 5A]
Compound No. 54
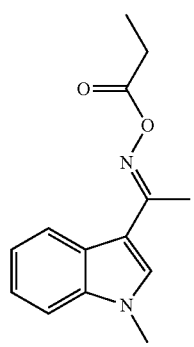
Compound No. 55
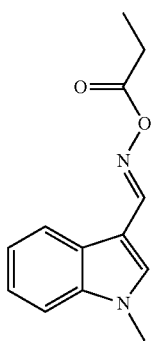
Compound No. 56
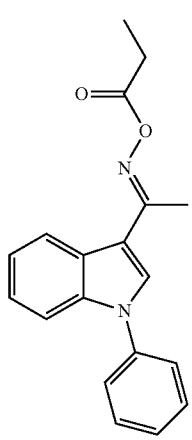
Compound No. 57
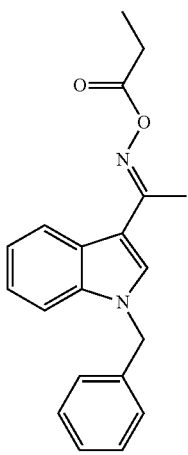
Compound No. 58
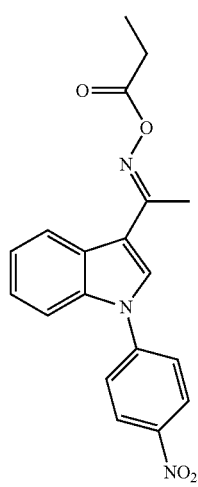
Compound No. 59
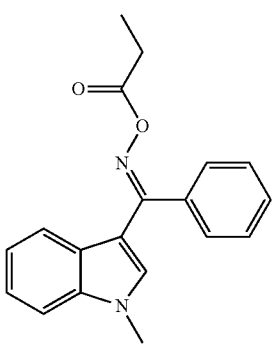

Compound No. 60
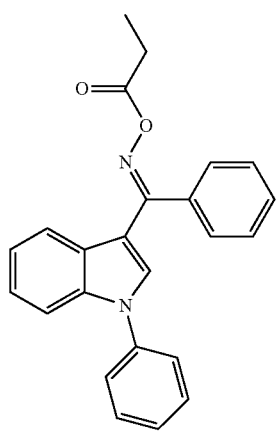
Compound No. 61
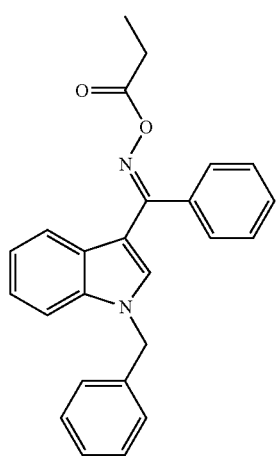
Compound No. 62
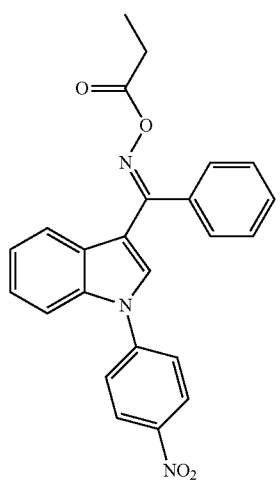
Compound No. 63
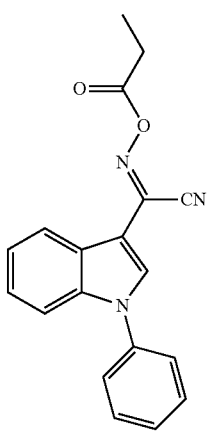
Compound No. 64
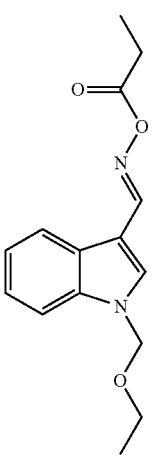
Compound No. 65
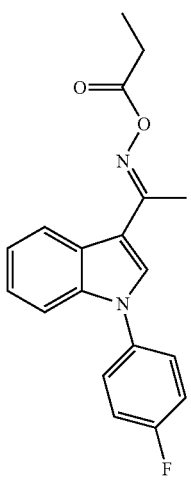

Compound No. 66
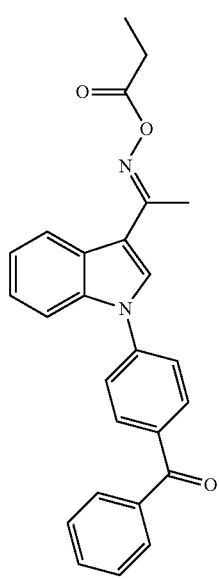
Compound No. 67
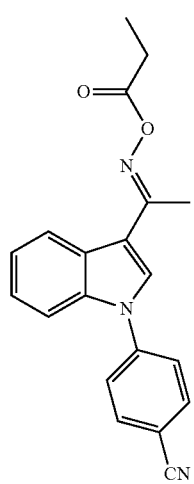
[Chem. 5B]
Compound No. 68
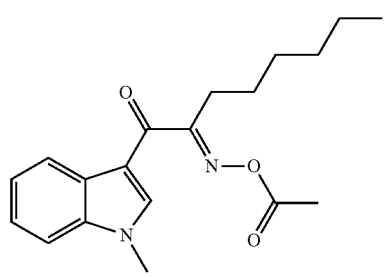
Compound No. 69
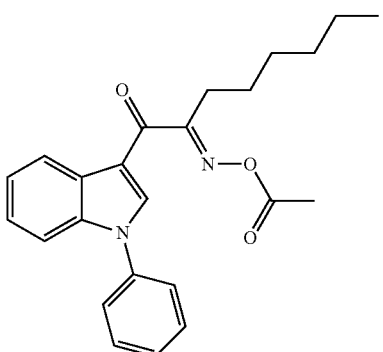
Compound No. 70
Compound No. 71
Compound No. 72
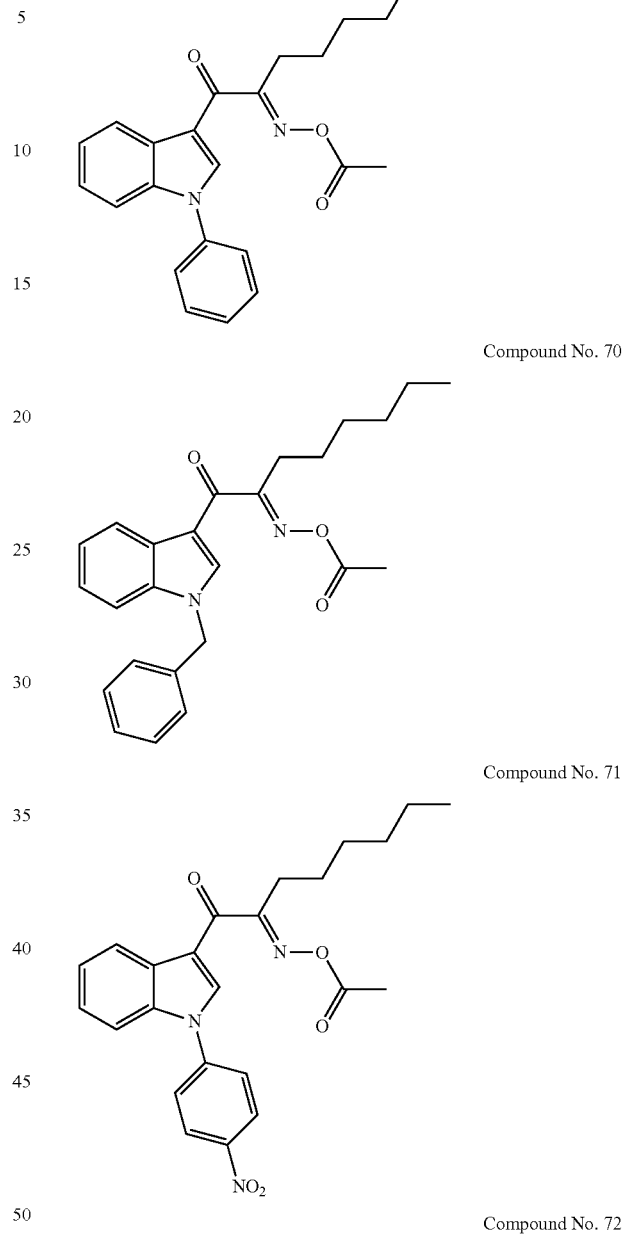

Compound No. 73
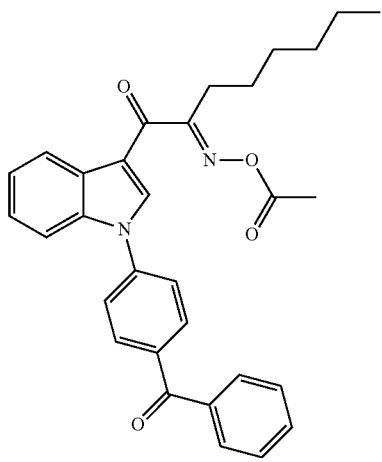
Compound No. 74
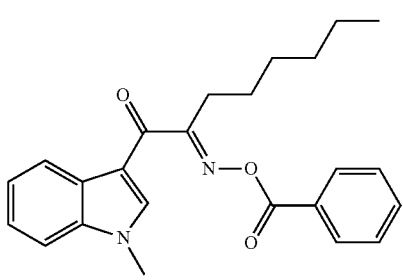
Compound No. 75
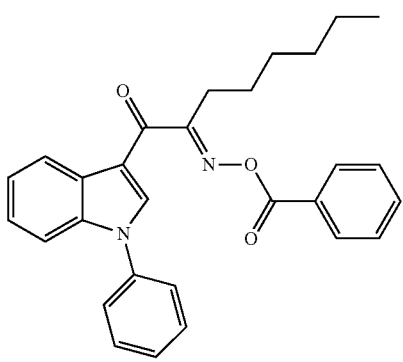
Compound No. 76
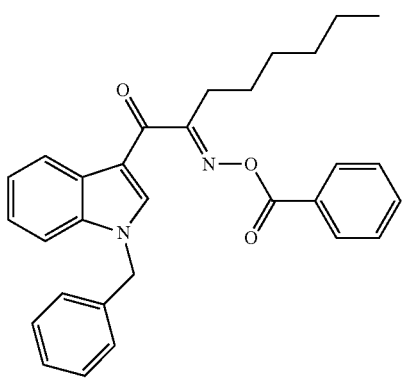
Compound No. 77
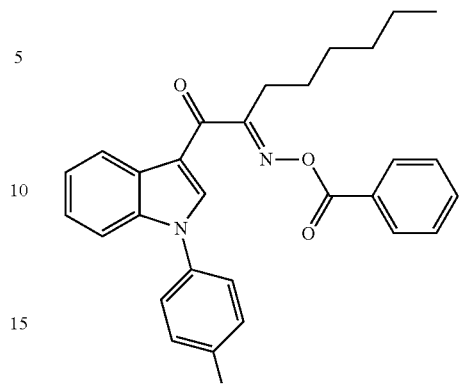
Compound No. 78
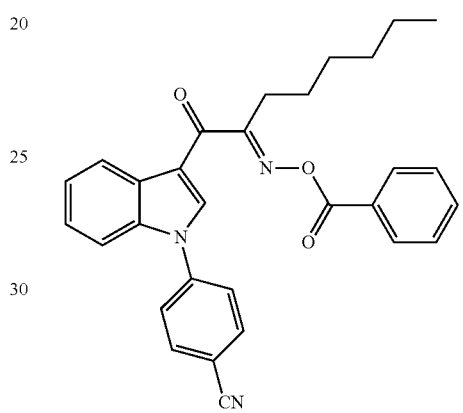
Compound No. 79
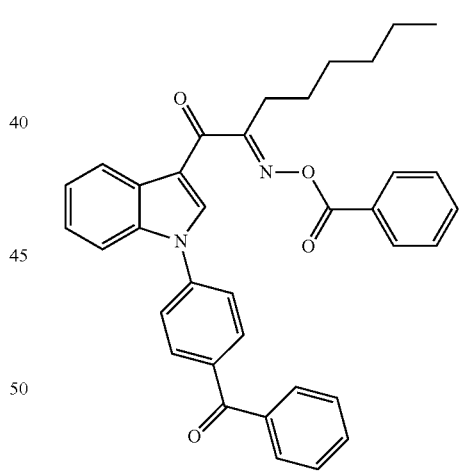
[Chem. 5C]
Compound No. 80
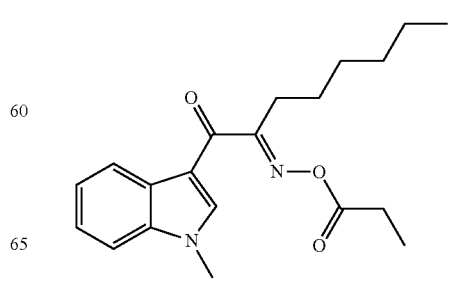

Compound No. 81
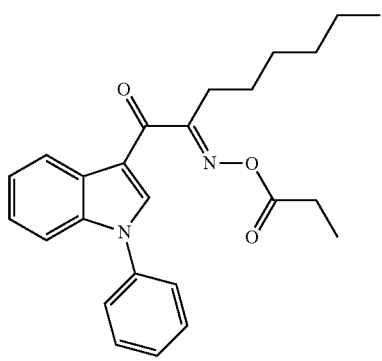
Compound No. 82
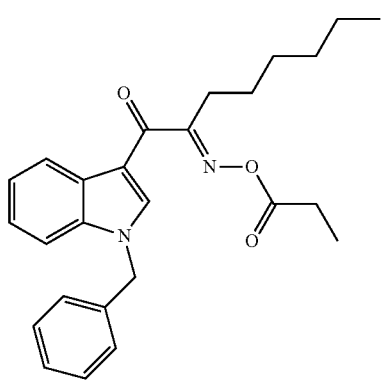
CompoundNo. 83
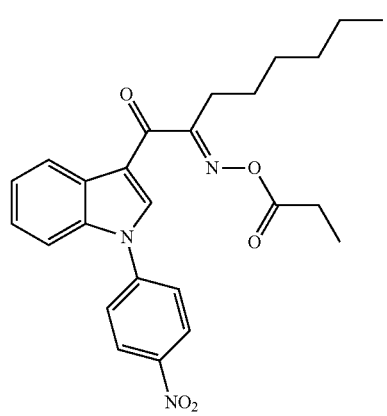
Compound No. 84
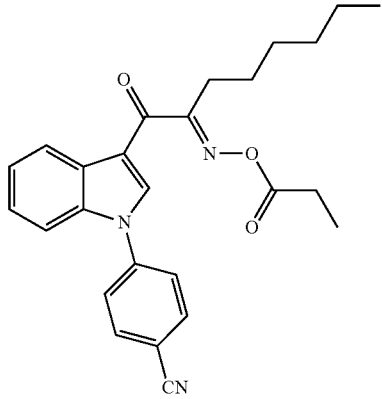
Compound No. 85
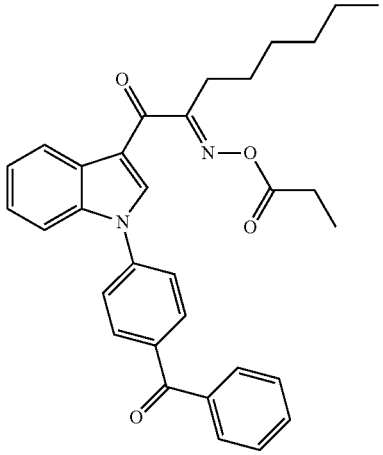
[Chem. 5D]
化合物 No. 86
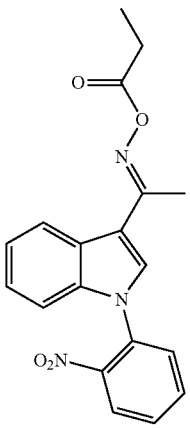
Compound No. 87
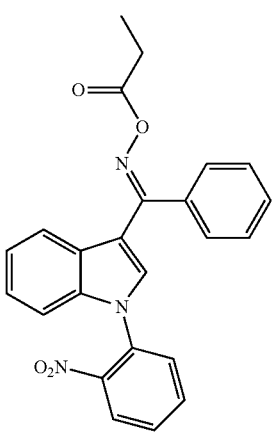

Compound No. 88
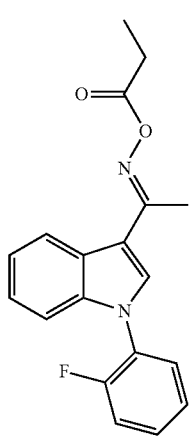
Compound No. 89
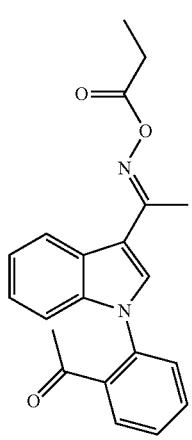
Compound No. 90
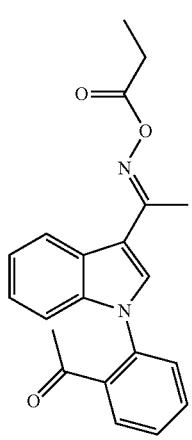
Compound No. 91
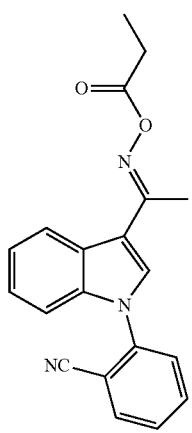
Compound No. 92
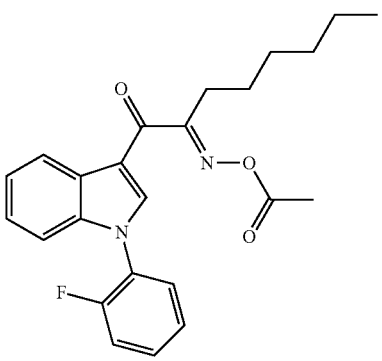
Compound No. 93
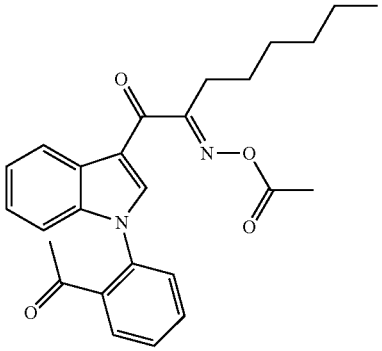
Compound No. 94
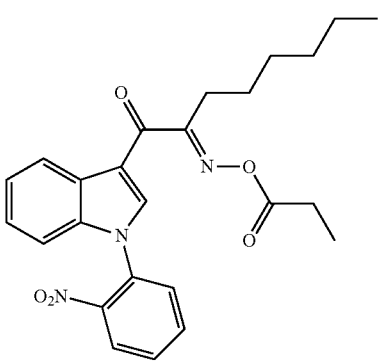
Compound No. 95
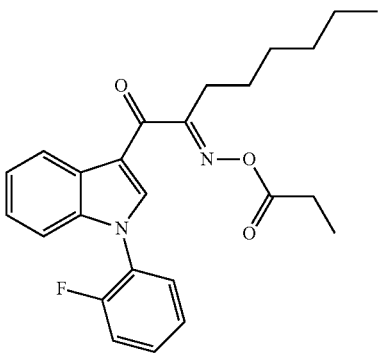

Compound No. 96
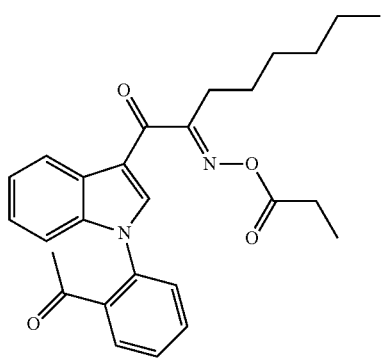
Compound No. 97
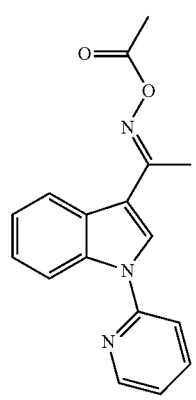
Compound No. 98
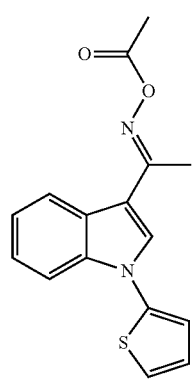
Compound No. 99
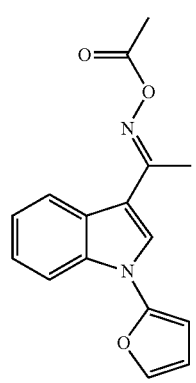
Compound No. 100
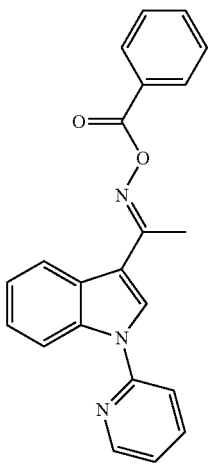
Compound No. 101
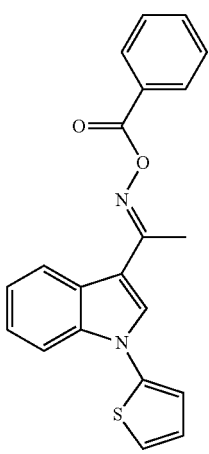
[Chem. 5E]
Compound No. 102
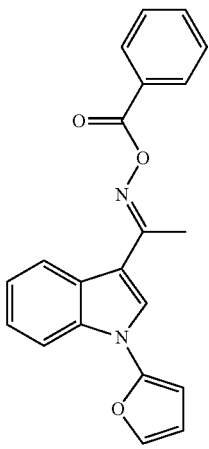

Compound No. 103
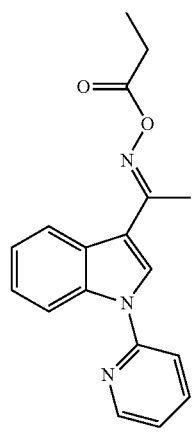
Compound No. 104
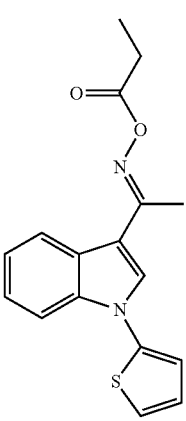
Compound No. 105
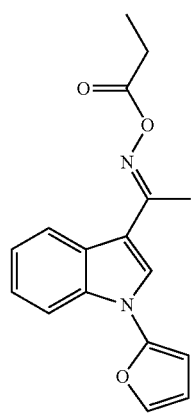
Compound No. 106
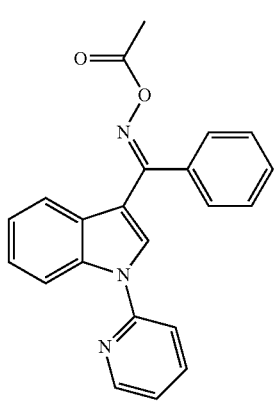
Compound No. 107
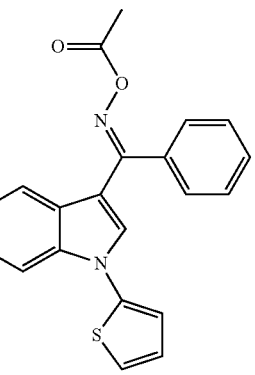
Compound No. 108
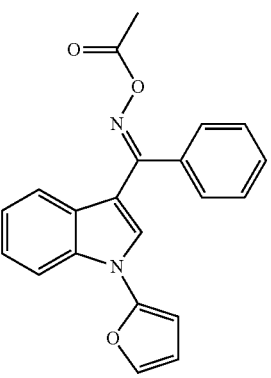
Compound No. 109
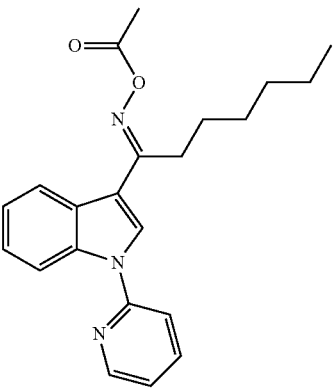
Compound No. 110
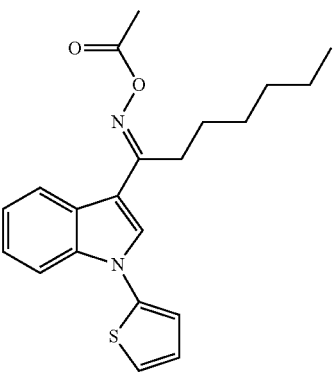

Compound No. 111
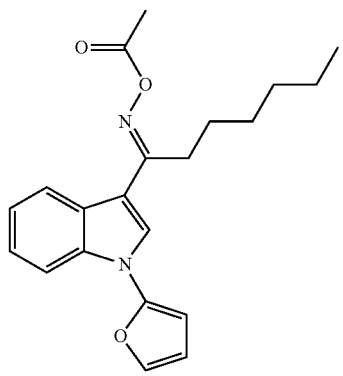
Compound No. 112
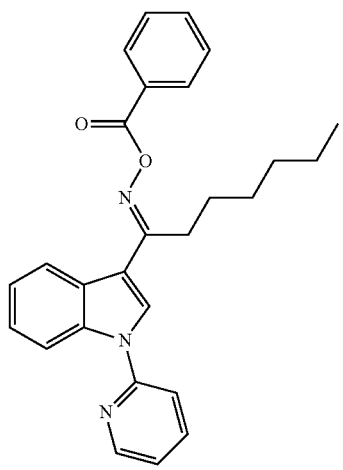
Compound No. 113
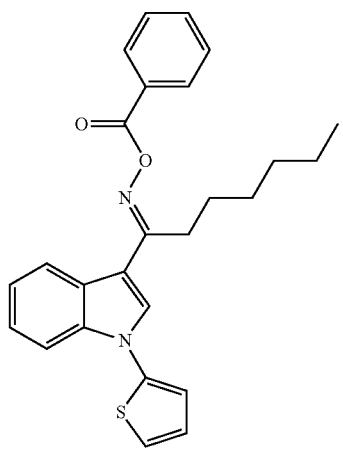
Compound No. 114
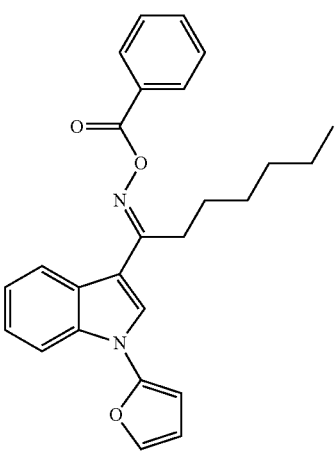
Compound No. 115
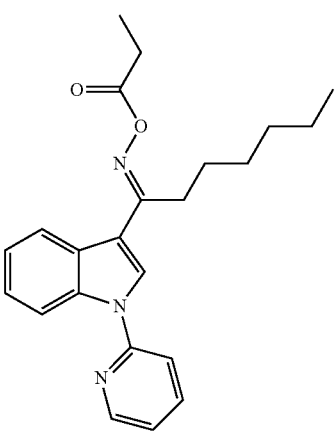
Compound No. 116
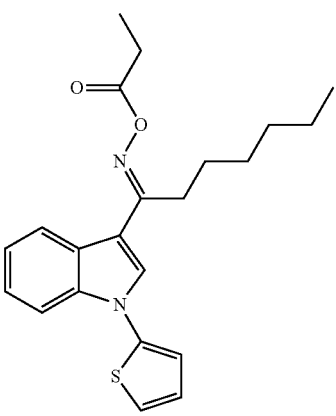

Compound No. 117
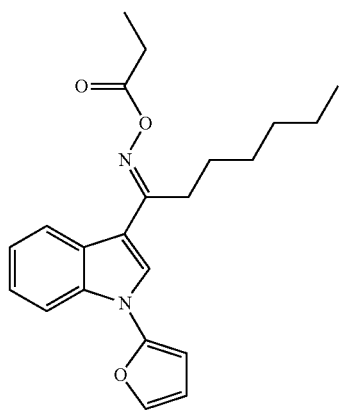
[Chem. 5F]
Compound No. 118
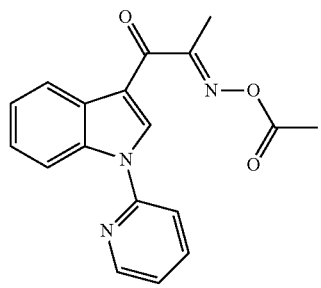
Compound No. 119
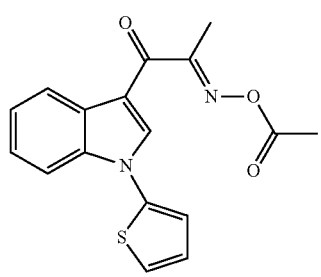
Compound No. 120
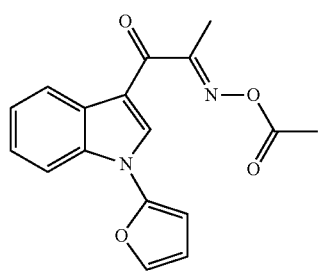
Compound No. 121
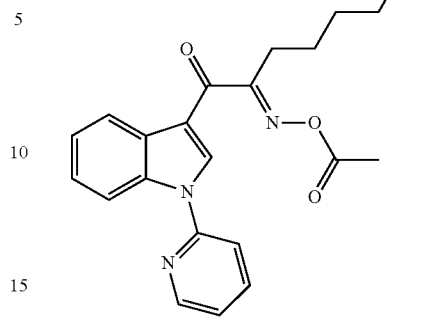
Compound No. 122
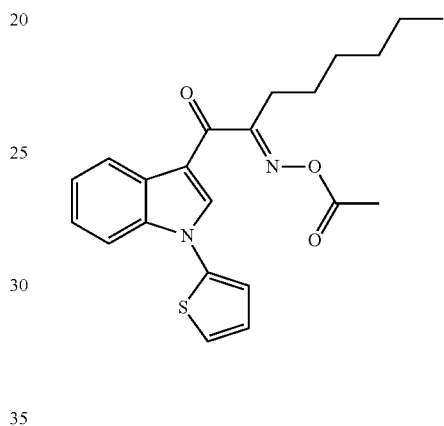
Compound No. 123
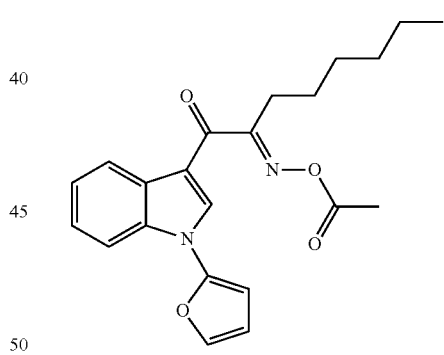
Compound No. 124
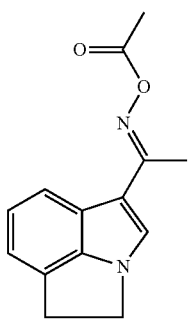

Compound No. 125
Compound No. 126
Compound No. 127
Compound No. 128
Compound No. 129
Compound No. 130
[Chem. 5G]
Compound No. 131
Compound No. 132
Compound No. 133
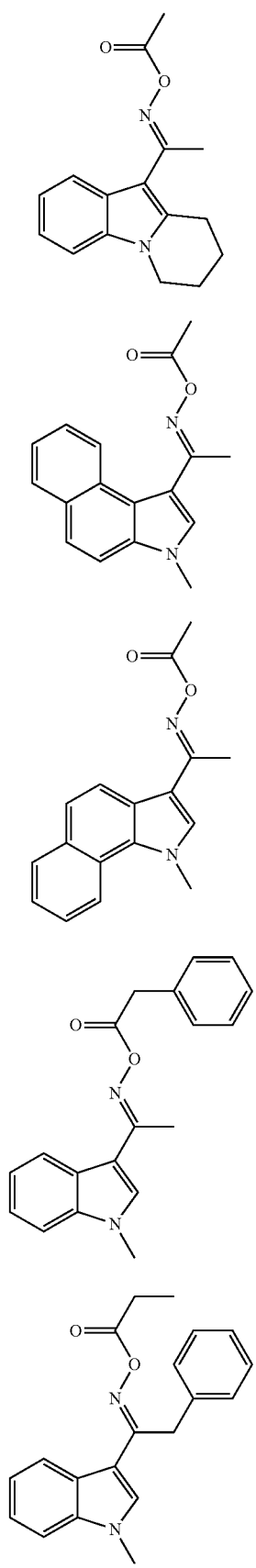
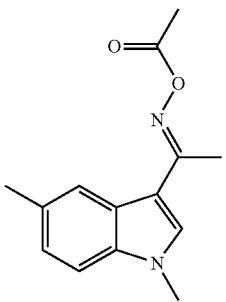

Compound No. 134
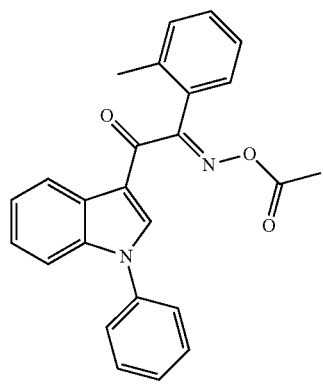
Compound No. 135
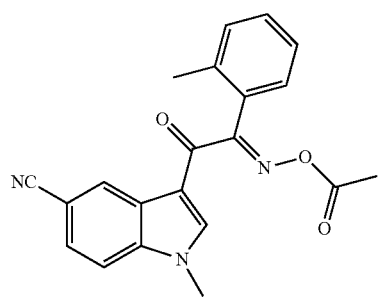
Compound No. 136
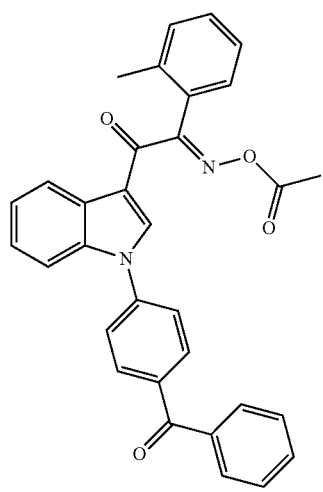
[Chem. 5H]
Compound No. 137
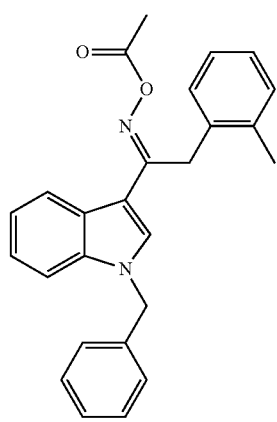
Compound No. 138
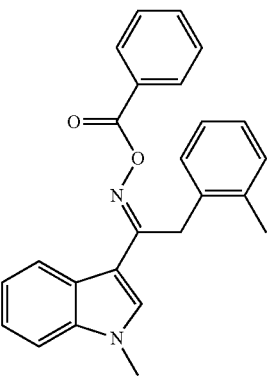
Compound No. 139
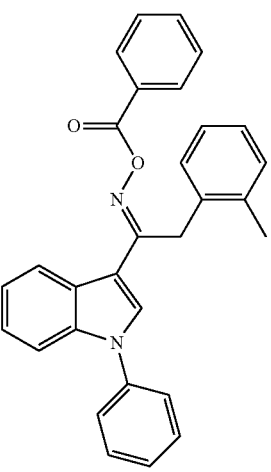
Compound No. 140
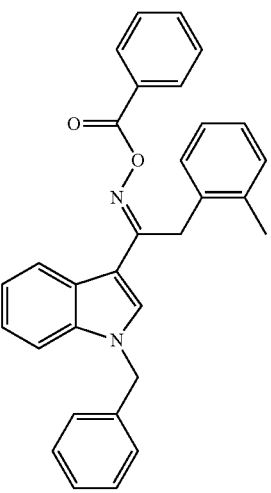

Compound No. 141
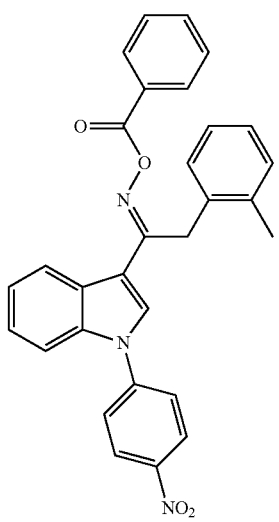
Compound No. 142
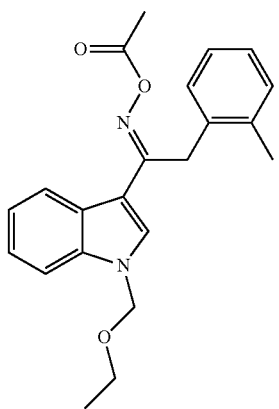
Compound No. 143
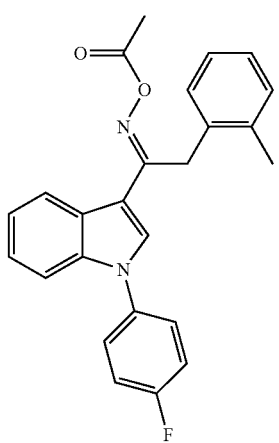
Compound No. 144
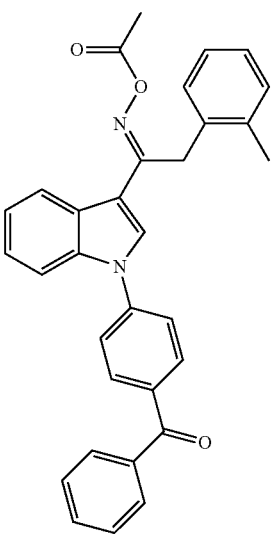
Compound No. 145
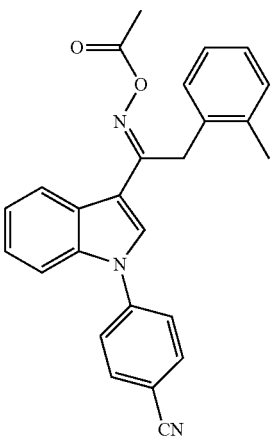
[Chem. 5I]
Compound No. 146
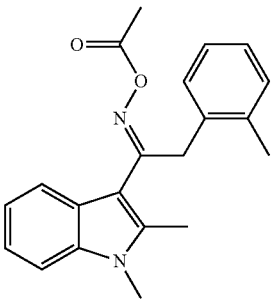
Compound No. 147
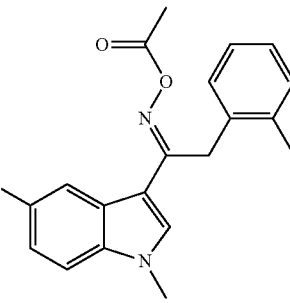

Compound No. 148

Compound No. 149

Compound No. 150

Compound No. 151

Compound No. 152

Compound No. 153

Compound No. 154

Compound No. 155

Compound No. 156

Compound No. 157

Compound No. 158
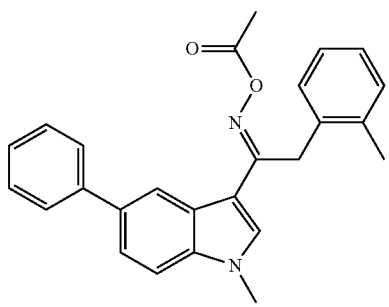
Compound No. 159
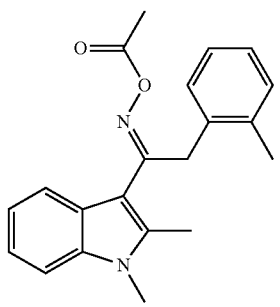
Compound No. 160
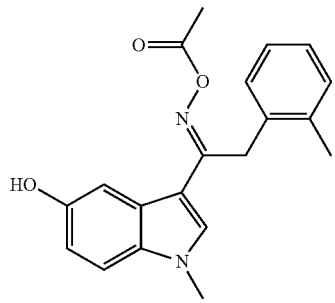
Compound No. 161
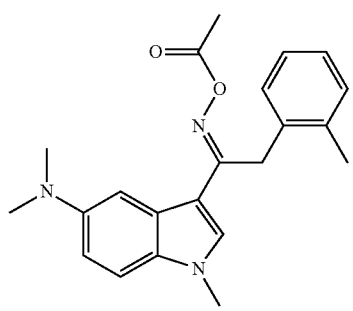
Compound No. 162
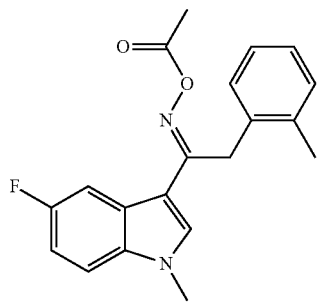
Compound No. 163
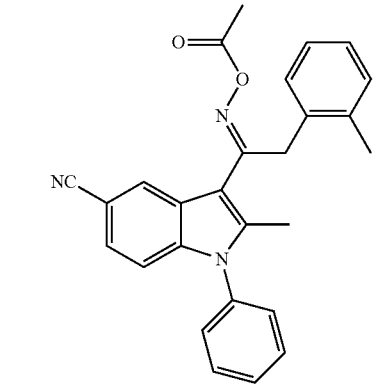
[Chem. 5J]
Compound No. 164
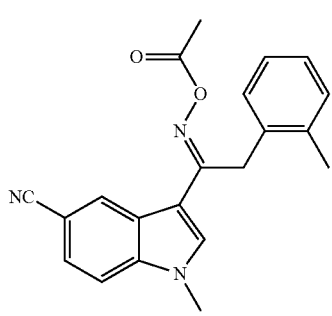
Compound No. 165
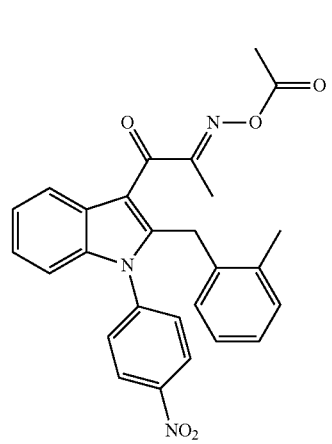
Compound No. 166
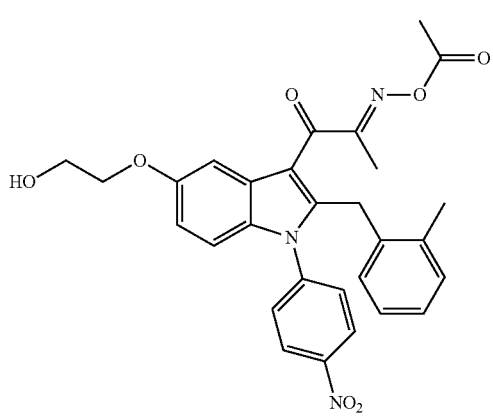

-continued
Compound No. 167
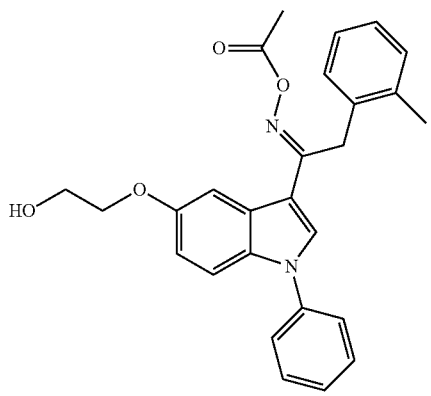
Compound No. 168
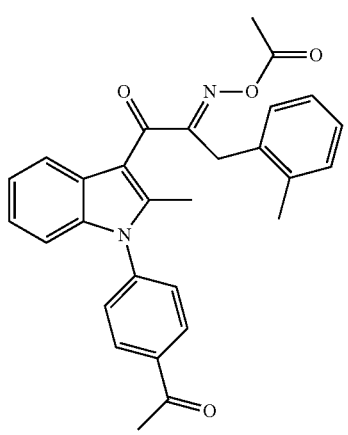
Compound No. 169
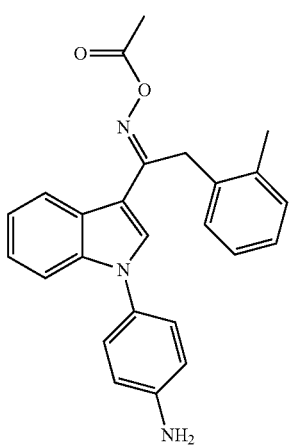
-continued
[Chem. 5K]
Compound No. 170
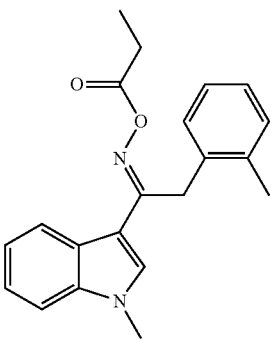
Compound No. 171
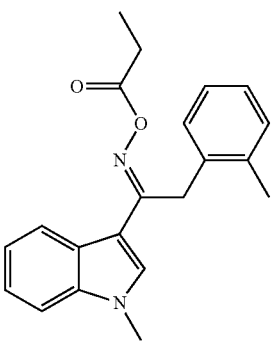
Compound No. 172
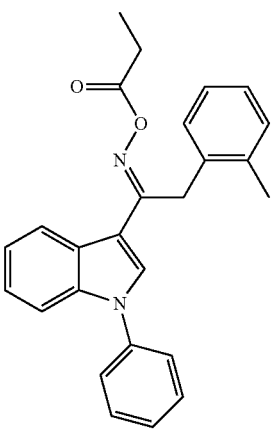
Compound No. 173
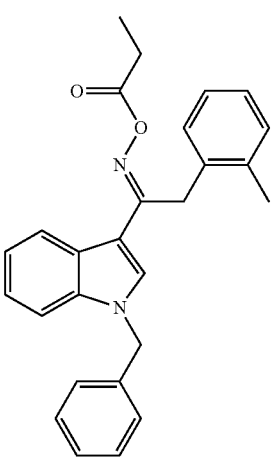

Compound No. 174
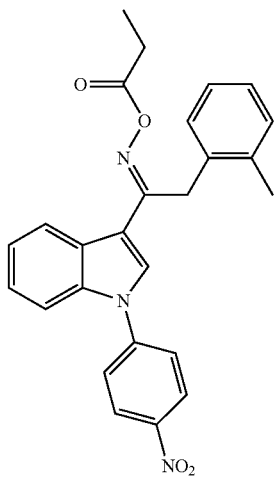
Compound No. 177
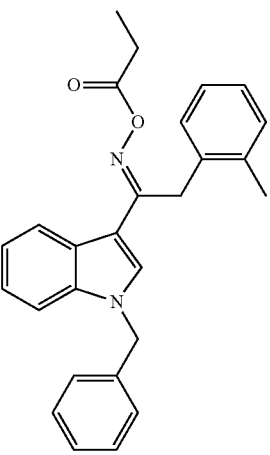
Compound No. 175
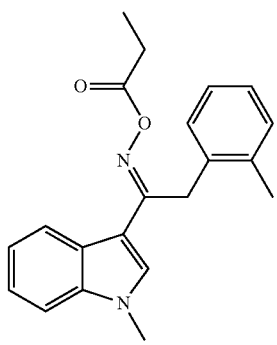
Compound No. 178
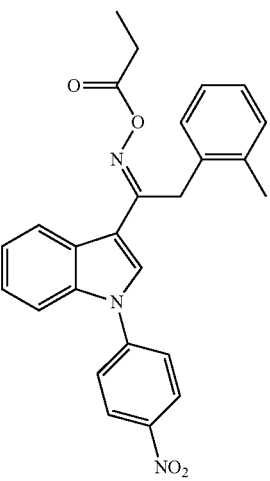
Compound No. 176
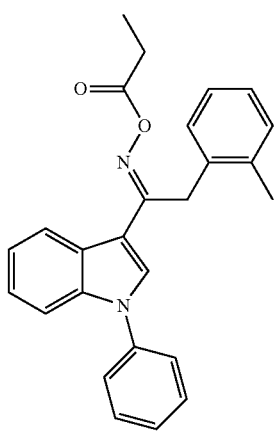
Compound No. 179
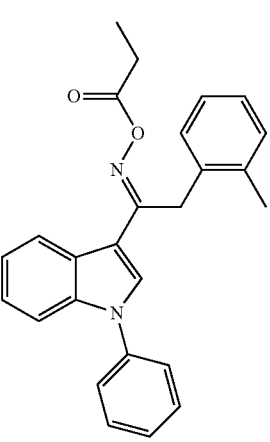

Compound No. 180
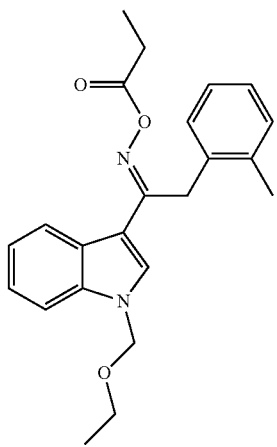
Compound No. 183
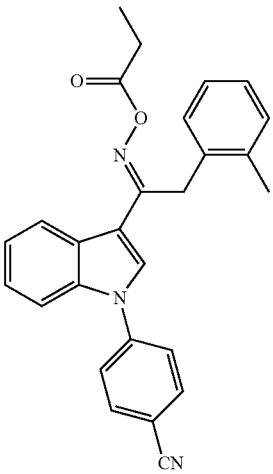
Compound No. 181
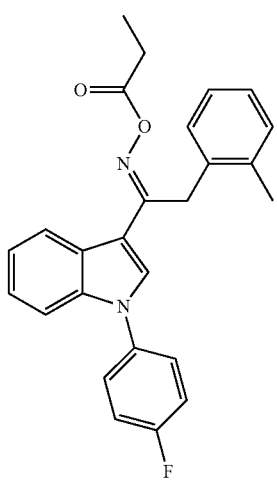
[Chem. 5L]
Compound No. 184
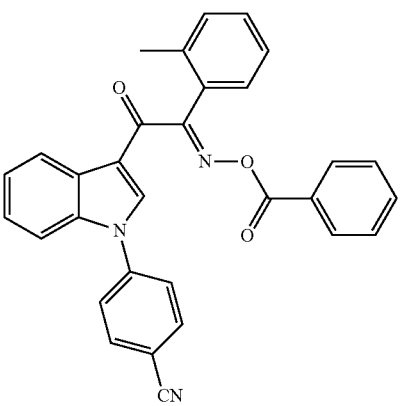
Compound No. 182
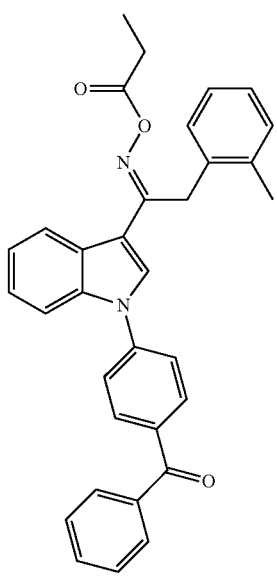
Compound No. 185
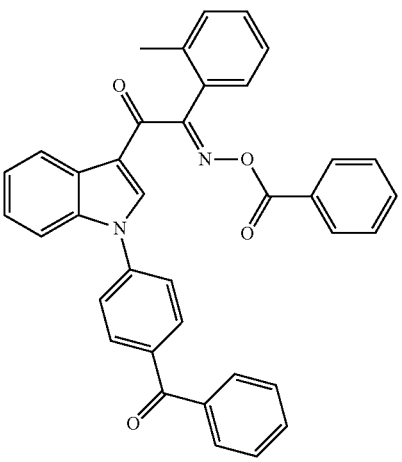

Compound No. 186
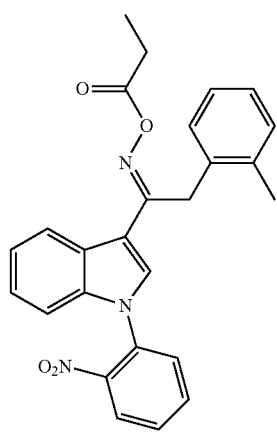
Compound No. 187
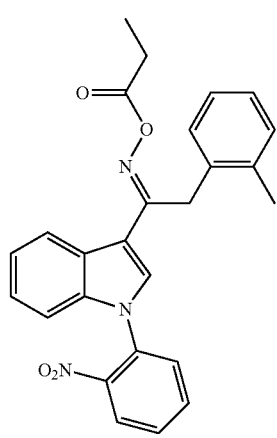
Compound No. 188
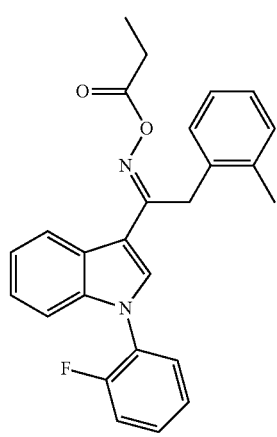
Compound No. 189
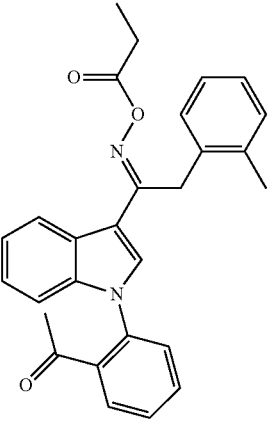
Compound No. 190
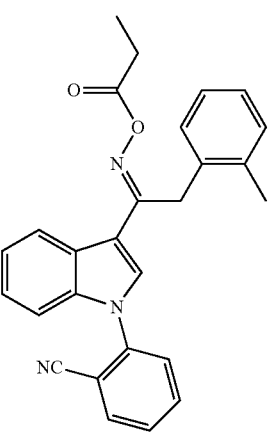
Compound No. 191
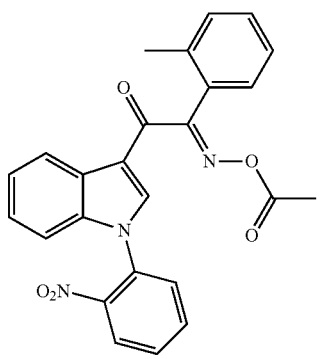
Compound No. 192
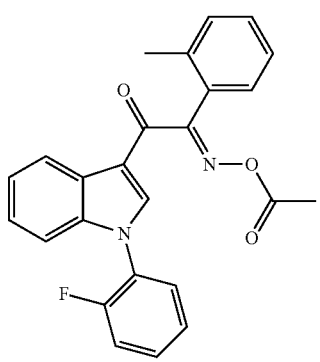

Compound No. 193
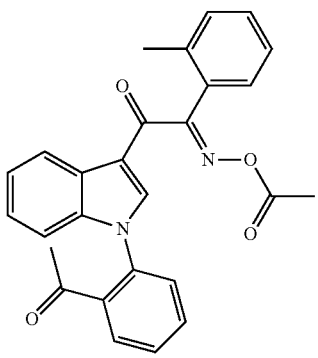
Compound No. 194
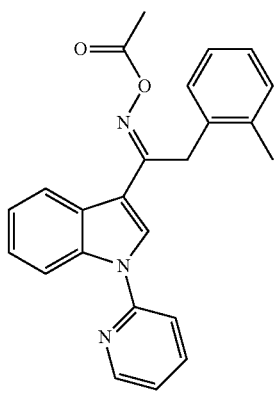
Compound No. 195
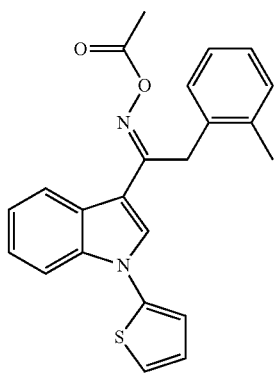
Compound No. 196
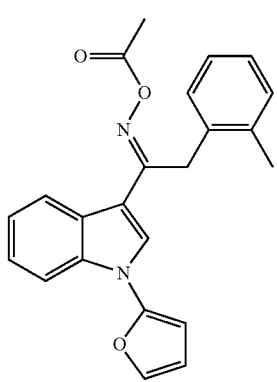
Compound No. 197
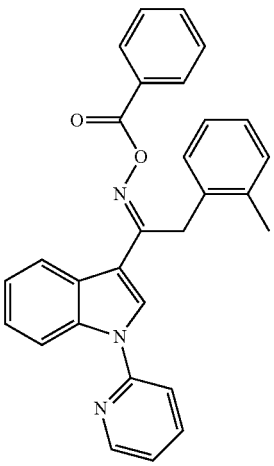
Compound No. 198
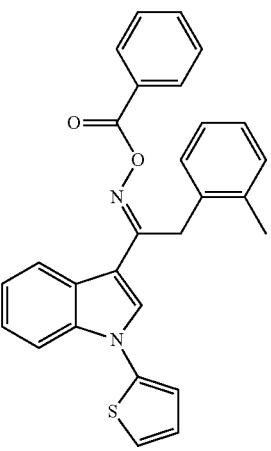
[Chem. 5M]
Compound No. 203
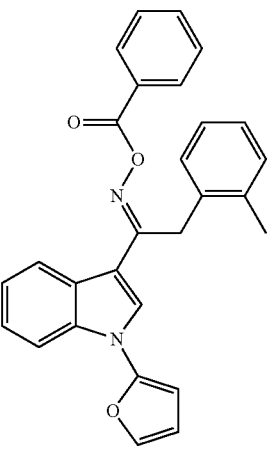

Compound No. 204
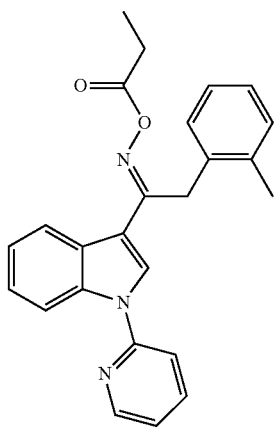
Compound No. 205
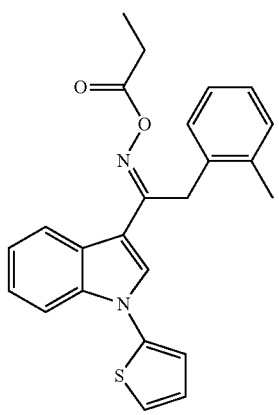
Compound No. 206
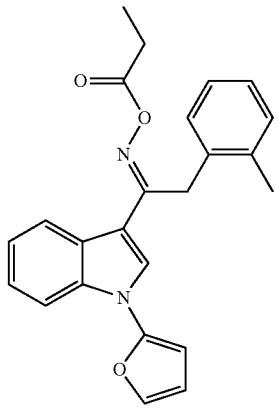
Compound No. 207
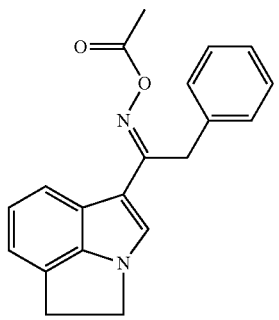
Compound No. 208
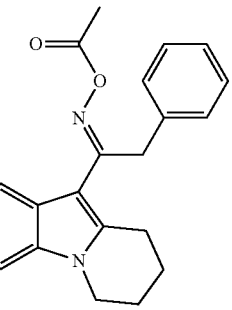
Compound No. 209
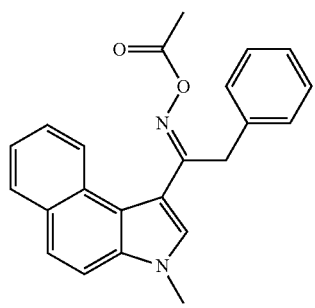
Compound No. 210
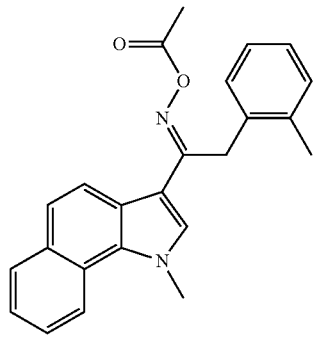
Compound No. 211
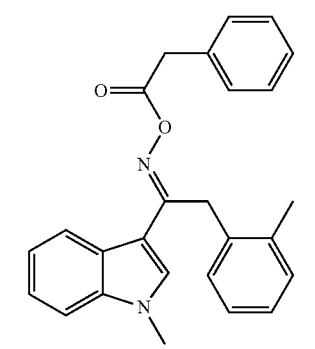
Compound No. 212
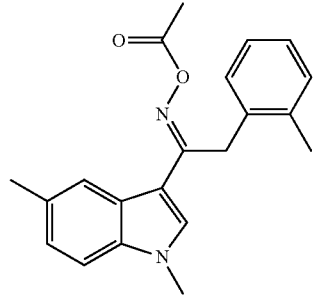

The oxime ester compound of formula (I) of the invention may be prepared by any available process, for example, the process described in JP 2000-80068A. Reaction scheme 1 shown below gives an example of available processes for preparing the oxime ester compound of formula (I) in which n=0. In this process, reaction between a ketone compound 1 and a halide gives a ketone compound 2, which is then allowed to react with hydroxylamine hydrochloride to form an oxime compound 3. The oxime compound 3 is then caused to react with an acid anhydride 4, an acid chloride 4', or a carboxylic acid salt 4" to yield an oxime ester compound of formula (I) of the invention. The compounds of formula (I) in which n=1 can also be prepared in a usual manner according to the process for preparing the compound in which n=0, for example, according to reaction scheme 2 below Reaction scheme 1:
[Chem. 6]

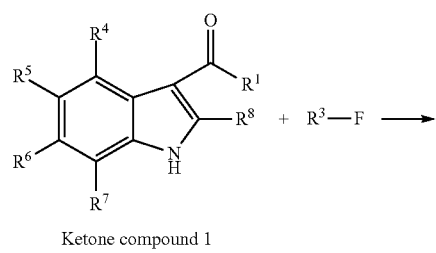

Ketone compound 1

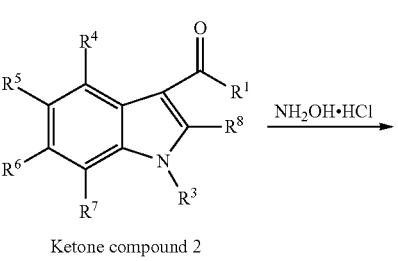

Ketone compound 2

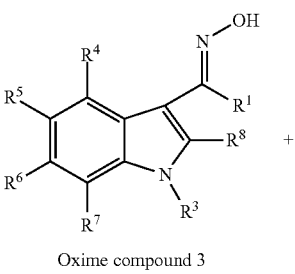

Oxime compound 3

Oxime compound 3 +

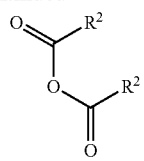

Acid anhydride 4 or

Acid anhydride 4' or

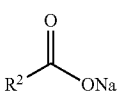

Carboxylic acid salt 4"

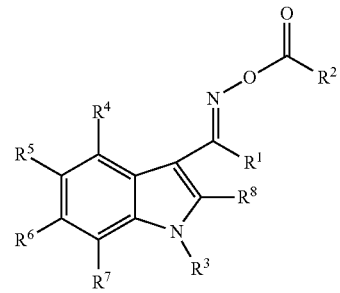

Oxime ester compound of invention wherein R¹, R², R³ R⁴, R⁵, R⁶, R⁷, and R⁸ are as defined for general formula (I).

Reaction scheme 2:
[Chem. 6A]

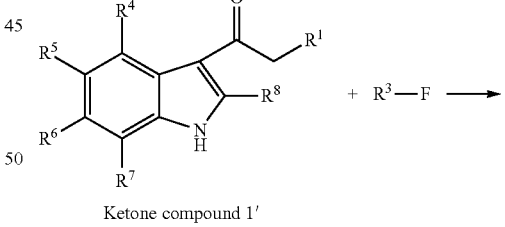

Ketone compound 1'

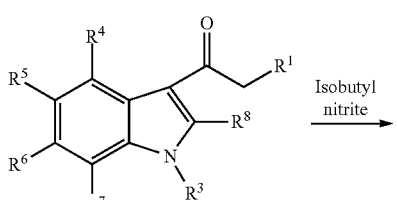

Ketone compound 2'

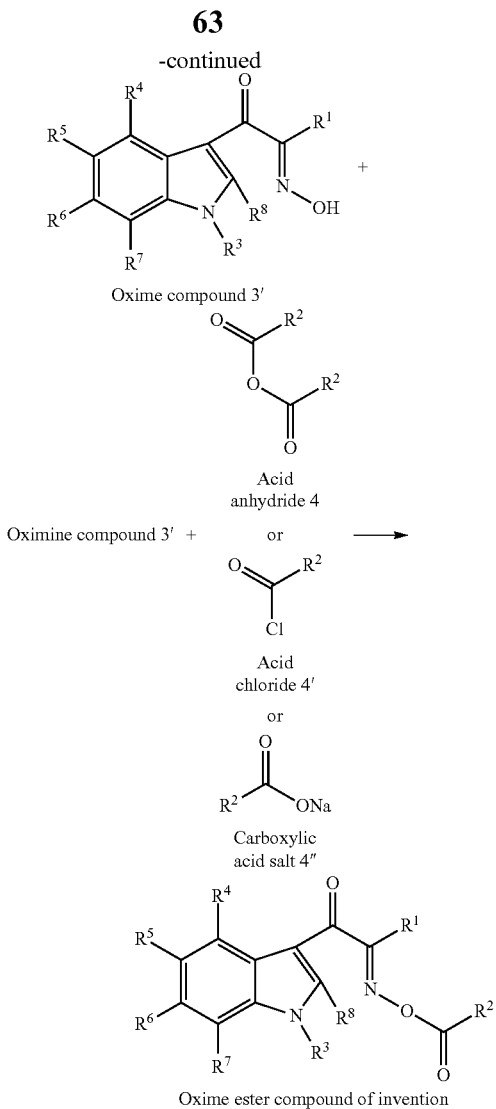

wherein $R^1$, $R^2$, $R^3$, $R^4$, $R^5$, $R^6$, $R^7$, and $R^8$ are as defined for general formula (I).

The above described novel oxime ester compound of the invention is useful as a radical polymerization initiator, especially a photopolymerization initiator or thermal polymerization initiator. The novel oxime ester compound of the invention is also useful as a sensitizer.

The photopolymerization initiator of the invention contains at least one oxime ester compound of the invention and is particularly useful for the photopolymerization of a polymerizable compound having an ethylenically unsaturated bond (hereinafter referred to as an ethylenically unsaturated polymerizable compound). The proportion of the oxime ester compound of the invention in the photopolymerization initiator of the invention is preferably 30% to 100% by mass, more preferably 50 to 100% by mass.

The photosensitive composition according to the invention essentially contains the photopolymerization initiator of the invention and an ethylenically unsaturated polymerizable compound and may optionally contain a compound having alkali developability and optionally having an ethylenically unsaturated group, an inorganic compound, a colorant, a solvent, and so forth in an appropriate combination.

The ethylenically unsaturated polymerizable compound for use in the invention is not particularly limited and may be selected from those conventionally used in photosensitive compositions. Examples include unsaturated aliphatic hydrocarbons, such as ethylene, propylene, butylene, isobutylene, vinyl chloride, vinylidene chloride, vinylidene fluoride, and tetrafluoroethylene; (meth)acrylic acid, α-chloroacrylic acid, itaconic acid, maleic acid, citraconic acid, fumaric acid, hymic acid, crotonic acid, isocrotonic acid, vinylacetic acid, allylacetic acid, cinnamic acid, sorbic acid, mesaconic acid, mono[2-(meth)acryloyloxyethyl] succinate, mono[2-(meth)acryloyloxyethyl] phthalate; a mono(methacrylate) of a polymer having a carboxyl group and a hydroxyl group at both terminals, such as ω-carboxypolycaprolactone mono(meth)acrylate; unsaturated polybasic acids, such as hydroxyethyl (meth)acrylate malate, hydroxypropyl (meth)acrylate malate, dicyclopentadiene malate, and a polyfunctional (meth)acrylate having one carboxyl group and two or more (meth)acryloyl groups; 2-hydroxyethyl (meth) acrylate, 2-hydroxypropyl (meth) acrylate, glycidyl (meth)acrylate, compounds A1 to A4 shown below, methyl (meth)acrylate, butyl (meth)acrylate, isobutyl (meth)acrylate, t-butyl (meth)acrylate, cyclohexyl (meth)acrylate, n-octyl (meth)acrylate, isooctyl (meth)acrylate, isononyl (meth)acrylate, stearyl (meth)acrylate, lauryl (meth)acrylate, methoxyethyl (meth) acrylate, dimethylaminomethyl (meth) acrylate, dimethylaminoethyl (meth) acrylate, aminopropyl (meth) acrylate, dimethylaminopropyl (meth) acrylate, ethoxyethyl (meth)acrylate, poly(ethoxy)ethyl (meth)acrylate, butoxyethoxyethyl (meth) acrylate, ethylhexyl (meth) acrylate, phenoxyethyl (meth) acrylate, tetrahydrofuryl (meth) acrylate, vinyl (meth)acrylate, allyl (meth)acrylate, benzyl (meth)acrylate; esters between an unsaturated monobasic acid and a polyhydric alcohol or polyhydric phenol, such as ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri (meth)acrylate, trimethylolpropane tri(meth)acrylate, dipentaerythritol hexa(meth)acrylate, dipentaerythritol penta(meth)acrylate, pentaerythritol tetra(meth)acrylate, pentaerythritol tri(meth)acrylate, tricyclodecanedimethylol di(meth)acrylate, tri[(meth)acryloylethyl] isocyanurate, and polyester (meth)acrylate oligomers; metal salts of unsaturated monobasic acids, such as zinc (meth)acrylate and magnesium (meth)acrylate; unsaturated polybasic acid anhydrides, such as maleic anhydride, itaconic anhydride, citraconic anhydride, methyltetrahydrophthalic anhydride, tetrahydrophthalic anhydride, trialkyltetrahydrophthalic anhydrides, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride; amides formed between an unsaturated monobasic acid and a polyfunctional amine, such as (meth)acrylamide, methylenebis (meth)acrylamide, diethylenetriaminetris(meth)acrylamide, xylylenebis(meth)acrylamide, α-chloroacrylamide, and N-2-hydroxyethyl (meth)acrylamide; unsaturated aldehydes, such as acrolein; unsaturated nitriles, such as (meth)acrylonitrile, α-chloroacrylonitrile, vinylidene cyanide, and allyl cyanide; unsaturated aromatic compounds, such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether; unsaturated ketones, such as methyl vinyl ketone; unsaturated amine compounds, such as vinylamine, allylamine, N-vinylpyrrolidone, and vinylpiperidine; vinyl alcohols, such as allyl alcohol and crotyl alcohol; vinyl ethers, such as vinyl methyl ether, vinyl ethyl ether, n-butyl vinyl ether, isobutyl vinyl ether, and allyl glycidyl ether; unsaturated imides, such as maleimide, N-phenylmaleimide, and N-cyclohexylmaleimide; indenes, such as indene and 1-methylindene; aliphatic conjugated dienes, such as 1,3-butadiene, isoprene, and chloroprene; macromonomers having a mono(meth)acryloyl group at the terminal of a polymeric molecular chain, such as polystyrene, polymethyl (meth) acrylate, poly-n-butyl (meth)acrylate, and polysiloxanes; vinyl chloride, vinylidene chloride, divinyl succinate, diallyl phthalate, triallyl phosphate, triallyl isocyanurate, vinyl thioether, vinylimidazole, vinyloxazoline, vinylcarbazole, vinylpyrrolidone, vinylpyridine, vinylurethane compounds formed between a hydroxyl-containing vinyl monomer and a polyisocyanate compound, and vinylepoxy compounds formed between a hydroxyl-containing vinyl monomer and a polyepoxy compound.

Of these ethylenically unsaturated polymerizable compounds, a (mono)methacrylate of a polymer having a carboxyl group and a hydroxyl group at both terminals, a polyfunctional (meth)acrylate having one carboxyl group and two or more (meth)acryloyl groups, and an ester between an unsaturated monobasic acid and a polyhydric alcohol or polyhydric phenol are suited to be polymerized by using the photopolymerization initiator containing the oxime ester compound of the invention.

The polymerizable compounds may be used either individually or in combination of two or more thereof. When two or more polymerizable compounds are used in combination, they may previously be copolymerized to be used as a copolymer.

[Chem. 7]

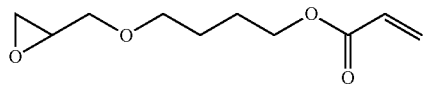

Compound A1

[Chem. 8]

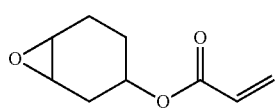

Compound A2

-continued

[Chem. 9]

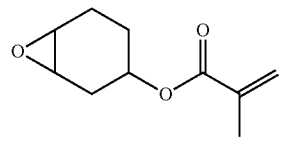

Compound A3

[Chem. 10]

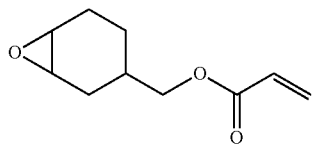

Compound A4

The compound having alkali developability (hereinafter referred to as an alkali-developable compound) and optionally having an ethylenically unsaturated group is not particularly limited as long as it is soluble in an aqueous alkali solution. The resins described in JP 2004-264414A can be exemplary compounds.

Additional examples of the alkali-developable compound optionally having ethylenically unsaturated group include acrylic ester copolymers, phenol and/or cresol novolak epoxy resins, polyphenylmethane epoxy resins having two or more epoxy groups, epoxy acrylate resins, and resins obtained by causing an unsaturated monobasic acid to react on the epoxy group of an epoxy compound, such as a compound represented by general formula (III) below, and causing the resulting reaction product to react with a polybasic acid anhydride. The epoxy acrylate resin as referred to above is a resin obtained by causing (meth)acrylic acid on the above described epoxy compound and is exemplified by Ripoxy SPC-2000, DICLITE UE-777 from DIC Corp., and Upika 4015 from U-Pica Co., Ltd.

Preferred of them are epoxy acrylate resins and resins obtained by causing an unsaturated monobasic acid to react on the epoxy group of an epoxy compound represented by general formula (III) and causing the resulting product to react with a polybasic acid anhydride.

The alkali-developable compound optionally having an ethylenically unsaturated bond preferably contains 0.2 to 1.0 equivalents of an unsaturated group.

[Chem. 11]

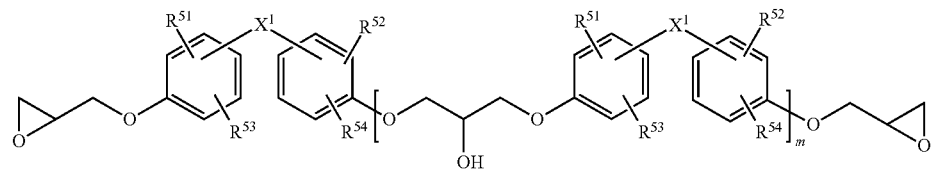

(III)

wherein $X^1$ represents a direct bond, a methylene group, a halogen-substituted or unsubstituted alkylidene group having 1 to 4 carbon atoms, an alicyclic hydrocarbon group having 3 to 20 carbon atoms, O, S, $SO_2$, SS, SO, CO, OCO, or a substituent represented by formula (α), (β), or (γ) below; $R^{51}$, $R^{52}$, $R^{53}$, and $R^{54}$ each independently represent a hydrogen atom, an alkyl group having 1 to 5 carbon atoms, an alkoxy group having 1 to 8 carbon atoms, an alkenyl group having 2 to 5 carbon atoms, or a halogen atom, the alkyl, alkoxy, and alkenyl being optionally substituted with a halogen atom; and m represents an integer of 0 to 10; when m=0, the compound may be any optical isomer.

[Chem. 12]

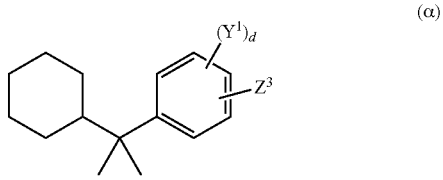

(α)

wherein $Z^3$ represents a hydrogen atom, a phenyl group optionally substituted with an alkyl group having 1 to 10 carbon atoms or an alkoxy group having 1 to 10 carbon atoms, or a cycloalkyl group having 3 to 10 carbon atoms optionally substituted with an alkyl group having 1 to 10 carbon atoms or an alkoxy group having 1 to 10 carbon atoms; $Y^1$ represents an alkyl group having 1 to 10 carbon atoms, an alkoxy group having 1 to 10 carbon atoms, an alkenyl group having 2 to 10 carbon atoms, or a halogen atom, the alkyl, alkoxy, and alkenyl being optionally substituted with a halogen atom; and d represents an integer of 0 to 5.

[Chem. 13]

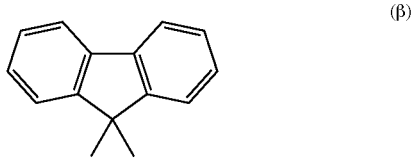

(β)

[Chem. 14]

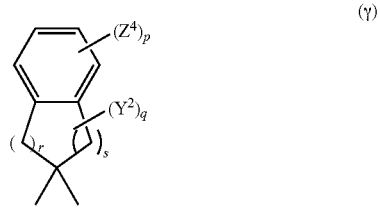

(γ)

wherein $Y^2$ and $Z^4$ each independently represent a halogen-substituted or unsubstituted alkyl group having 1 to 10 carbon atoms, a halogen-substituted or unsubstituted aryl group having 6 to 20 carbon atoms, a halogen-substituted or unsubstituted aryloxy group having 6 to 20 carbon atoms, a halogen-substituted or unsubstituted arylthio group having 6 to 20 carbon atoms, a halogen-substituted or unsubstituted arylalkenyl group having 6 to 20 carbon atoms, a halogen-substituted or unsubstituted arylalkyl group having 7 to 20 carbon atoms, a halogen-substituted or unsubstituted heterocyclic group having 2 to 20 carbon atoms, or a halogen atom; the alkylene moiety of the alkyl and arylalkyl group may be interrupted by an unsaturated bond, —O—, or —S—; a plurality of $Z^4$ adjacent to each other may be connected to form a ring; p represents an integer of 0 to 4; q represents an integer of 0 to 8; r represents an integer of 0 to 4; s represents an integer of 0 to 4; and the sum of r and s is an integer of 2 to 4.

Examples of the unsaturated monobasic acid that is caused to react on the epoxy compound include acrylic acid, methacrylic acid, crotonic acid, cinnamic acid, sorbic acid, hydroxyethyl methacrylate malate, hydroxyethyl acrylate malate, hydroxypropyl methacrylate malate, hydroxypropyl acrylate malate, and dicyclopentadiene malate.

Examples of the polybasic acid anhydride that is caused to react after the reaction of the unsaturated monobasic acid include biphenyltetracarboxylic acid dianhydride, tetrahydrophthalic anhydride, succinic anhydride, biphthalic anhydride, maleic anhydride, trimellitic anhydride, pyromellitic anhydride, 2,2',3,3'-benzophenonetetracarboxylic acid anhydride, ethylene glycol bisanhydrotrimellitate, glycerol trisanhydrotrimellitate, hexahydrophthalic anhydride, methyltetrahydrophthalic anhydride, nadic anhydride, methylnadic anhydride, trialkyltetrahydrophthalic anhydrides, hexahydrophthalic anhydride, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride.

The epoxy compound, unsaturated monobasic acid, and polybasic acid anhydride are preferably used in the following molar ratios. The epoxy compound and the unsaturated monobasic acid are preferably used in a molar ratio that results in the formation of an epoxy adduct having 0.1 to 1.0 carboxyl group of the unsaturated monobasic acid added per epoxy group of the epoxy compound. The polybasic acid anhydride is preferably used in such a molar ratio as to provide 0.1 to 1.0 acid anhydride structure per hydroxyl group of the epoxy adduct.

The reactions of the epoxy compound, unsaturated monobasic acid, and polybasic acid anhydride are carried out in a usual manner.

The alkali-developable photosensitive resin composition, which is an embodiment of the photosensitive composition of the invention, essentially contains the photopolymerization initiator of the invention, a polymerizable compound having an ethylenically unsaturated bond, and the alkali-developable compound optionally having an ethylenically unsaturated group and may optionally contain an inorganic compound, a colorant, a solvent, and so forth in an appropriate combination. The alkali-developable photosensitive resin composition of the invention which contains a colorant is particularly referred to as a colored alkali-developable photosensitive resin composition of the invention.

The ethylenically unsaturated polymerizable compound and the alkali-developable compound optionally having an ethylenically unsaturated bond for use in the alkali-developable photosensitive resin composition may be the same or different. They may be used either individually or in combination of two or more thereof.

In order to improve alkali developability of the (colored) alkali-developable photosensitive resin composition of the invention by adjusting the acid value, the alkali-developable compound optionally having an ethylenically unsaturated bond may be used in combination with a mono- or polyfunctional epoxy compound. It is preferred that the solid content of the alkali-developable compound optionally having an ethylenically unsaturated bond have an acid value of 5 to 120 mgKOH/g. The amount of the mono- or polyfunctional epoxy compound to be used is preferably decided so as to satisfy the above recited range of acid value.

Examples of the monofunctional epoxy compound include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxyglycidyl ether, p-butylphenyl glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexene monoxide, 1,2-epoxy-4-vinylcyclohexane, styrene oxide, pinene oxide, methylstyrene oxide, cyclohexene oxide, propylene oxide, and compounds A2 and A3 shown above.

It is preferable to use, as the polyfunctional epoxy compound, at least one compound selected from the group consisting of bisphenol epoxy compounds and glycidyl ethers. Using at least one of them is effective in providing a (colored) alkali developable photosensitive resin composition having further improved characteristics.

Examples of the bisphenol epoxy compounds include the epoxy compounds represented by general formula (III) described supra and others including hydrogenated bisphenol epoxy compounds.

Examples of the glycidyl ethers include ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri (glycidyloxymethypethane, 1,1,1-tri(glycidyloxymethy) methane, and 1,1,1,1-tetra(glycidyloxymethyl)methane.

Other useful polyfunctional epoxy compounds include novolak epoxy compounds, such as phenol novolak epoxy compounds, biphenyl novolak epoxy compounds, cresol novolak epoxy compounds, bisphenol A novolak epoxy compounds, and dicyclopentadiene novolak epoxy compounds; alicyclic epoxy compounds, such as 3,4-epoxy-6-methylcyclohexylmethyl 3,4-epoxy-6-methylcyclohexanecarboxylate, 3,4-epoxycyclohexylmethyl 3,4-epoxycyclohexanecarboxylate, and 1-epoxyethyl-3,4-epoxycyclohexane; glycidyl esters, such as diglycidyl phthalate, diglycidyl tetrahydrophthalate, and glycidyl dimerate; glycidylamines, such as tetraglycidyl diaminodiphenylmethane, triglycidyl p-aminophenol, and N,N-diglycidylaniline; heterocyclic epoxy compounds, such as 1,3-diglycidyl-5,5-dimethylhydantoin and triglycidyl isocyanurate; dioxide compounds, such as dicyclopentadiene dioxide; naphthalene epoxy compounds, triphenylmethane epoxy compounds, and dicyclopentadiene epoxy compounds.

The amount of the photopolymerization initiator of the invention to be used in the photosensitive composition of the invention is preferably, but not limited to, 1 to 70 parts, more preferably 1 to 50 parts, even more preferably 5 to 30 parts, by mass per 100 parts by mass of the ethylenically unsaturated polymerizable compound.

When the photosensitive composition of the invention is formulated as a (colored) alkali-developable photosensitive resin composition, the content of the alkali-developable compound optionally having an ethylenically unsaturated bond in the (colored) alkali-developable photosensitive resin composition is preferably 1 to 20 mass %, more preferably 3 to 12 mass %.

If desired, the photosensitive composition of the invention may contain a solvent. Usually, solvents capable of dissolving or dispersing the above described components (including the photopolymerization initiator of the invention, the ethylenically unsaturated polymerizable compound, and so on) are used. Such solvents include ketones, e.g., methyl ethyl ketone, methyl amyl ketone, diethyl ketone, acetone, methyl isopropyl ketone, methyl isobutyl ketone, cyclohexanone, and 2-heptanone; ethers, such as ethyl ether, dioxane, tetrahydrofuran, 1,2-dimethoxyethane, 1,2-diethoxyethane, and dipropylene glycol dimethyl ether; esters, such as methyl acetate, ethyl acetate, n-propyl acetate, isopropyl acetate, n-butyl acetate, cyclohexyl acetate, ethyl lactate, dimethyl succinate, and Texanol; cellosolves, such as ethylene glycol monomethyl ether and ethylene glycol monoethyl ether; alcohols, such as methanol, ethanol, isopropyl alcohol, n-propanol, isobutanol, n-butanol, and amyl alcohol; ether esters, such as ethylene glycol monomethyl ether acetate, ethylene glycol monoethyl ether acetate, propylene glycol 1-monomethyl ether 2-acetate, dipropylene glycol monomethyl ether acetate, 3-methoxybutyl ether acetate, and ethoxyethyl ether propionate; BTX solvents (benzene, toluene, xylene, etc.); aliphatic hydrocarbons, such as hexane, heptane, octane, and cyclohexane; terpene hydrocarbon oils, such as turpentine oil, D-limonene, and pinene; paraffinic solvents, such as mineral spirit, Swazol #310 (from Cosmo Matsuyama Oil Co., ltd.), and Solvesso #100 (from Exxon Chemical); halogenated aliphatic hydrocarbons, such as carbon tetrachloride, chloroform, trichloroethylene, methylene chloride, and 1,2-dichloroethane; halogenated aromatic hydrocarbons, such as chlorobenzene; carbitol solvents, aniline, triethylamine, pyridine, acetic acid, acetonitrile, carbon disulfide, N,N-dimethylformamide, N,N-dimethylacetamide, N-methylpyrrolidone, dimethyl sulfoxide, and water. These solvents may be used either individually or in the form of a mixture of two or more thereof.

Preferred of them are ketones and ether esters, particularly propylene glycol 1-monomethyl ether 2-acetate, cyclohexanone, and so on in view of providing improved compatibility between a resist and the photopolymerization initiator in the photosensitive composition.

The photosensitive composition, particularly the alkali-developable photosensitive resin composition of the invention may be formulated as a colored (alkali developable) photosensitive composition by addition of a colorant. Examples of the colorant include pigments, dyes, and naturally occurring dyes. The colorants may be used either individually or as a mixture of two or more thereof.

Useful pigments may be either organic or inorganic and include nitroso compounds, nitro compounds, azo compounds, diazo compounds, xanthene compounds, quinoline compounds, anthraquinone compounds, coumarin compounds, phthalocyanine compounds, isoindolinone compounds, isoindoline compounds, quinacridone compounds, anthanthrone compounds, peiynone compounds, perylene compounds, diketopyrrolopyrrole compounds, thioindigo compounds, dioxazine compounds, triphenylmethane compounds, quinophthalone compounds, naphthalenetetracarboxylic acids; metal complex compounds, such as azo dyes and cyanine dyes; lake pigments; carbon blacks, such as furnace black, channel black, thermal black, acetylene black, Ketjen black, and lamp black; the carbon blacks recited having been modified or coated with an epoxy resin; the carbon blacks having been dispersed in a solvent together with a resin to have 20 to 200 mg/g of the resin adsorbed thereon, the carbon blacks having been surface treated with an acid or an alkali, carbon black having an average particle size of 8 nm or greater and a DBP absorption of 90 ml/100 g or less, carbon black having a total oxygen content of 9 mg or more per 100 m$^2$ of its surface area as calculated from the CO and CO$_2$ content in the volatile content at 950° C.; graphite, graphitized carbon black, activated carbon, carbon fiber, carbon nanotube, carbon microcoil, carbon nanohorn, carbon aerogel, fullerene; aniline black, pigment black 7, titanium black; chromium oxide green, Milori blue, cobalt green, cobalt blue, manganese compounds, ferrocyanides, phosphate ultramarine blue, Prussian blue, ultramarine, cerulean blue, viridian, emerald green, lead sulfate, lead yellow, zinc yellow, Bengal red (red iron (III) oxide), cadmium red, synthetic iron black, and amber. The pigments may be used either individually or in the form of a mixture thereof.

Commercially available pigments may be used, including pigment red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; pigment orange 13, 31, 34, 36, 38, 43, 46, 48, 49, 51, 52, 55, 59, 60, 61, 62, 64, 65, and 71; pigment yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; pigment green 7, 10, and 36; pigment blue 15, 15:1, 15:2, 15:3, 15:4, 15:5, 15:6, 22, 24, 56, 60, 61, 62, and 64; and pigment violet 1, 19, 23, 27, 29, 30, 32, 37, 40, and 50.

Examples of the dyes include azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes, and cyanine dyes. These may be used in the form of a mixture thereof.

The amount of the colorant, if added to the photosensitive composition, is preferably 50 to 350 parts, more preferably 100 to 250 parts, by mass per 100 parts by mass of the ethylenically unsaturated polymerizable compound.

The photosensitive composition of the invention may further contain an inorganic compound. Examples of the inorganic compound include metal oxides, such as nickel oxide, iron oxide, iridium oxide, titanium oxide, zinc oxide, magnesium oxide, calcium oxide, potassium oxide, silica, and alumina; layered clay minerals, Milori blue, calcium carbonate, magnesium carbonate, cobalt compounds, manganese compounds, glass powder (particularly glass frit), mica, talc, kaolin, ferrocyanides, various metal sulfates, sulfides, selenides, aluminum silicate, calcium silicate, aluminum hydroxide, platinum, gold, silver, and copper.

Preferred of them are glass frit, titanium oxide, silica, layered clay minerals, and silver. The content of the inorganic compound in the photosensitive composition of the invention is preferably 0.1 to 1000 parts, more preferably 10 to 800 parts, by mass per 100 parts by mass of the ethylenically unsaturated polymerizable compound. The inorganic compounds may be used either individually or in combination of two or more thereof.

The inorganic compounds are used as, for example, a filler, an antireflection agent, an electrically conductive agent, a stabilizer, a flame retardant, a mechanical strength improving agent, a specific wavelength absorbing agent, an ink repellent agent, and the like.

The photosensitive composition of the invention may contain a dispersant for the colorant and/or the inorganic compound. Any dispersant may be used as long as it is capable of dispersing and stabilizing the colorant or the inorganic compound. Commercially available dispersants, for example, BYK series available from BYK Chemie GmbH, may be used. Polymeric dispersants comprising a polyester, polyether, or polyurethane having a basic functional group and dispersants having a nitrogen atom as a basic functional group, the functional group having a nitrogen atom being an amine and/or a quaternary salt thereof, and having an amine value of 1 to 100 mgKOH/g are preferably used.

The photosensitive composition of the invention may contain, in addition to the oxime ester compound of the invention, other photopolymerization initiators that may be conventionally known compounds. Examples of the other initiators include benzophenone, phenyl biphenyl ketone, 1-hydroxy-1-benzoylcyclohexane, benzoin, benzyl dimethyl ketal, 1-benzyl-1-dimethylamino-1-(4'-morpholinobenzoyl) propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1,7-bis(9'-acridinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyp-s-triazine, 2,2-bis(2-chlorophenyl)-4,5,4',5'-tetraphenyl-1,2 biimidazole, 4,4-azobisisobutyronitrile, triphenylphosphine, camphorquinone; N-1414, N-1717, N-1919, NCI-831, and NCI-930 (from ADEKA Corp.); Irgacure 369, Irgacure 907, Irgacure OXE 01, and Irgacure OXE 02 (from BASF); benzoyl peroxide; and compounds represented by general formulae (IV) shown below. The amount of the photopolymerization initiator other than the oxime ester compounds of the invention, if used, is preferably not more than equivalent to the mass of the oxime ester compound of the invention. The above recited other photopolymerization initiators can be used either individually or in a combination of two or more thereof.

[Chem. 17]

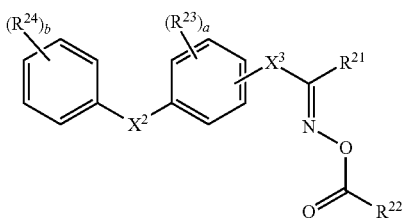

(IV)

wherein $R^{21}$ and $R^{22}$ each independently represent a hydrogen atom, a cyano group, an alkyl group having 1 to 20 carbon atoms, an aryl group having 6 to 30 carbon atoms, an arylalkyl group having 7 to 30 carbon atoms, or a heterocyclic group having 2 to 20 carbon atoms;

$R^{23}$ and $R^{24}$ each independently represent a halogen atom, a nitro group, a cyano group, a hydroxyl group, a carboxyl group, $R^{25}$, $OR^{26}$, $SR^{27}$, $NR^{28}R^{29}$, $COR^{30}$, $SOR^{31}$, $SO_2R^{32}$, or $CONR^{33}R^{34}$, $R^{23}$ and $R^{24}$ may be taken together to form a ring;

$R^{25}$, $R^{26}$, $R^{27}$, $R^{28}$, $R^{29}$, $R^{30}$, $R^{31}$, $R^{32}$, $R^{33}$, and $R^{34}$ each independently represent an alkyl group having 1 to 20 carbon atoms, an aryl group having 6 to 30 carbon atoms, an arylalkyl group having 7 to 30 carbon atoms, or a heterocyclic group having 2 to 20 carbon atoms;

$X^2$ represents an oxygen atom, a sulfur atom, a selenium atom, $CR^{35}R^{36}$, CO, $NR^{37}$, or $PR^{38}$;

$X^3$ represents a single bond or CO;

$R^{21}$, $R^{22}$, $R^{25}$, $R^{26}$, $R^{27}$, $R^{28}$, $R^{29}$, $R^{30}$, $R^{35}$, $R^{36}$, $R^{37}$ and $R^{38}$ each independently represent an alkyl group having 1 to 20 carbon atoms, an aryl group having 6 to 30 carbon atoms, or an arylalkyl group having 7 to 30 carbon atoms, the methylene moiety of the alkyl or arylalkyl group being optionally substituted with a halogen atom, a nitro group, a cyano group, a hydroxyl group, a carboxyl group or a heterocyclic group and being optionally interrupted by —O—;

$R^{39}$, $R^{40}$, $R^{41}$ and $R^{42}$ may each independently form a ring together with either one of the adjacent benzene rings;

a represents an integer of 0 to 4; and b represents an integer of 0 to 5.

The photosensitive composition of the invention may contain a latent additive represented by general formula (A), (B), or (C):

[Chem. 17A]

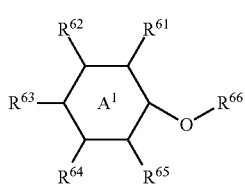

(A)

wherein ring $A^1$ represents a 6-membered alicyclic, aromatic, or heterocyclic ring; $R^{61}$, $R^{62}$, $R^{63}$, $R^{64}$, and $R^{65}$ each represent a hydrogen atom, a halogen atom, a cyano group, a hydroxyl group, a nitro group, a carboxyl group, or an optionally substituted C1-C40 alkyl group, C6-C20 aryl group, C7-C20 arylalkyl group, C2-C20 heterocyclic ring-containing group, or —O—$R^{66}$; at least one of $R^{61}$, $R^{62}$, $R^{63}$, $R^{64}$, and $R^{65}$ is not hydrogen; $R^{66}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group.

[Chem. 17B]

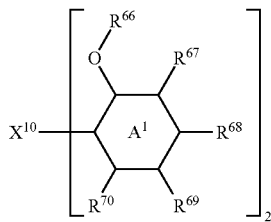

wherein $X^{10}$ represents a group having general formula (1) below; $R^{67}$, $R^{68}$, $R^{69}$, and $R^{70}$ each represent a hydrogen atom, a halogen atom, a cyano group, a hydroxyl group, a nitro group, a carboxyl group, or an optionally substituted C1-C40 alkyl group, C6-C20 aryl group, C7-C20 arylalkyl group, or C2-C20 heterocyclic ring-containing group; at least one of $R^{67}$, $R^{68}$, $R^{69}$, and $R^{70}$ is not hydrogen; ring $A^1$ and $R^{66}$ are as defined above for general formula (A).

[Chem. 17C]

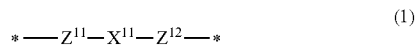

(1)

wherein $X^{11}$ represents —$CR^{71}R^{72}$—, —$NR^{73}$—, a divalent C1-C35 aliphatic hydrocarbon group, a divalent C6-C35 aromatic hydrocarbon group, a divalent C2-C35 heterocyclic group, or a substituent having partial structural formula (i), (ii), or (iii) below, the aliphatic hydrocarbon group being optionally interrupted by —O—, —S—, —CO—, —COO—, —OCO—, —NH—, or a plurality of these interrupting groups linked together provided that no two oxygen atoms are connected to each other; $R^{71}$ and $R^{72}$ each represent a hydrogen atom, a C1-C8 alkyl group, a C6-C20 aryl group, or a C7-C20 arylalkyl group; $Z^{11}$ and $Z^{12}$ each independently represent a direct bond, —O—, —S—, —CO—, —CO—O—, —O—CO—, —$SO_2$—, —SS—, —SO—, or —$NR^{74}$—; and $R^{73}$ and $R^{74}$ each represent a hydrogen atom, an optionally substituted C1-C35 aliphatic hydrocarbon group, an optionally substituted C6-C35 aromatic hydrocarbon group, or an optionally substituted C2-C35 heterocyclic group.

[Chem. 17D]

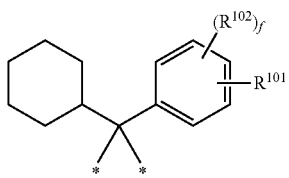

(i)

wherein $R^{101}$ represents a hydrogen atom, or an optionally substituted phenyl group or C3-C10 cycloalkyl group; $R^{102}$ represents a C1-C10 alkyl group, a C1-C10 alkoxy group, a C2-C10 alkenyl group, or a halogen atom, the alkyl, alkoxy, and alkenyl groups being optionally substituted; and f represents an integer of 0 to 5.

[Chem. 17E]

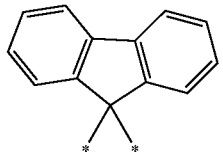

(ii)

[Chem. 17F]

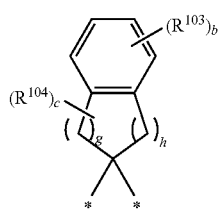

(iii)

wherein $R^{103}$ and $R^{104}$ each independently represent an optionally substituted C1-C10 alkyl group, an optionally substituted C6-C20 aryl group, an optionally substituted C6-C20 aryloxy group, an optionally substituted C6-C20 arylthio group, an optionally substituted C6-C20 arylalkenyl group, an optionally substituted C7-C20 arylalkyl group, an optionally substituted C2-C20 heterocyclic group, or a halogen atom, the methylene moiety of the alkyl and arylalkyl groups being optionally interrupted by an unsaturated bond, —O—, or —S—; two adjacent $R^{103}$'s may be taken together to form a ring; b represents a number of 0 to 4; c represents a number of 0 to 8; g represents a number of 0 to 4; and h represents a number of 0 to 4, provided that the sum of g and h is 2 to 4.

[Chem. 17G]

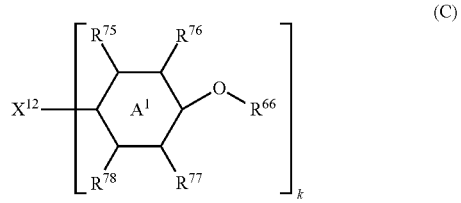

(C)

wherein m is 2 to 6; $X^{12}$ represents a group having general formula (1) above when m=2, a group having general formula (2) below when m=3, a group having general formula (3) below when in=4, a group having general formula (4) below when m=5, or a group having general formula (5) below when m=6; $R^{75}$, $R^{76}$, $R^{77}$, and $R^{78}$ each represent a hydrogen atom, a halogen atom, a cyano group, a hydroxyl group, a nitro group, a carboxyl group, or an optionally substituted C1-C40 alkyl group, C6-C20 aryl group, C7-C20 arylalkyl group, or C2-C20 heterocyclic ring-containing group, provided that at least one of $R^{75}$, $R^{76}$, $R^{77}$, and $R^{78}$ is not a hydrogen atom; and ring $A^1$ and $R^{66}$ are as defined for general formula (A).

[Chem. 17H]

(2)

wherein $Y^{11}$ represents a trivalent C3-C35 aliphatic hydrocarbon group, a trivalent C3-C35 alicyclic hydrocarbon group, a trivalent C6-C35 aromatic hydrocarbon group, or a trivalent C2-C35 heterocyclic group; $Z^{11}$, $Z^{12}$, and $Z^{13}$ each independently represent a direct bond, —O—, —S—, —CO—, —CO—O—, —O—CO—, —SO$_2$—, —SS—, —SO—, —NR$^{79}$—, —PR$^{79}$—, an optionally substituted C1-C35 aliphatic hydrocarbon group, an optionally substituted C6-C35 aromatic hydrocarbon group, or an optionally substituted C2-C35 heterocyclic group; and $R^{79}$ represents a hydrogen atom, an optionally substituted C1-C35 aliphatic hydrocarbon group, an optionally substituted C6-C35 aromatic hydrocarbon group, or an optionally substituted C2-C35 heterocyclic group, the aliphatic hydrocarbon group being optionally interrupted by a carbon-carbon double bond, —O—, —CO—, —O—CO—, —CO—O—, or —SO$_2$—.

[Chem. 17I]

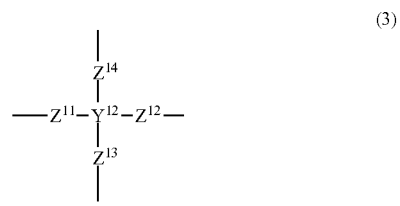

(3)

wherein $Y^{12}$ represents a carbon atom or a tetravalent, C1-C35 aliphatic, C6-C35 aromatic, or C2-C35 heterocyclic group, the aliphatic hydrocarbon group being optionally interrupted by —COO—, —O—, —OCO—, —NHCO—, —NH—or —CONH—; and $Z^{11}$, $Z^{12}$, $Z^{13}$, and $Z^{14}$ independently have the same meaning as $Z^{11}$, $Z^{12}$, and $Z^{13}$ in general formula (2).

[Chem. 17J]

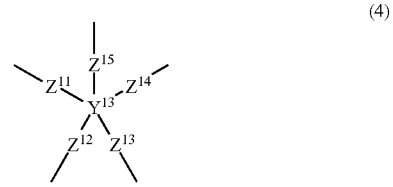

(4)

wherein $Y^{13}$ represents a tetravalent, C2-C35 aliphatic, C6-C30 aromatic, or C2-C30 heterocyclic group, the aliphatic hydrocarbon group being optionally interrupted by —COO—, —O—, —OCO—, —NHCO—, —NH—, or —CONH—; and $Z^{11}$, $Z^{12}$, $Z^{13}$, $Z^{14}$, and $Z^{15}$ independently have the same meaning as $Z^{11}$, $Z^{12}$, and $Z^{13}$ in general formula (2).

[Chem. 17K]

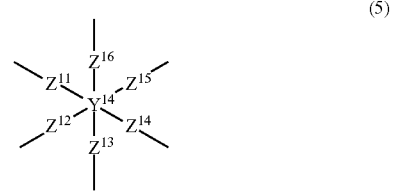

(5)

wherein $Y^{14}$ represents a hexavalent, C2-C35 aliphatic, C6-C35 aromatic, or C2-C35 heterocyclic group, the aliphatic hydrocarbon group being optionally interrupted by —COO—, —O—, —OCO—, —NHCO—, —NH—, or —CONH—; and $Z^{11}$, $Z^{12}$, $Z^{13}$, $Z^{14}$, $Z^{15}$, and $Z^{16}$ independently have the same meaning as $Z^{11}$, $Z^{12}$, and $Z^{13}$ in general formula (2).

If desired, the photosensitive composition of the invention may contain commonly used additives, including thermal polymerization retarders (e.g., p-anisole, hydroquinone, pyrocatechol, t-butylcatechol, and phenothiazine), plasticizers, adhesion accelerators, fillers, anti-foaming agents, leveling agents, surface modifiers, antioxidants, ultraviolet absorbers, dispersing aids, anti-coagulants, catalysts, effect accelerators, crosslinking agents, and thickeners.

The amounts of the optional components other than the ethylenically unsaturated polymerizable compound and the oxime ester compound of the invention, except the above described other photopolymerization initiator, alkali-developable compound optionally having an ethylenically unsaturated group, inorganic compound (filler), colorant, and solvent, in the photosensitive composition are decided as appropriate to the intended use of the components. Preferably, the total amount of these optional components is not more than 50 parts by mass per 100 parts by mass of the ethylenically unsaturated polymerizable compound.

The photosensitive composition of the invention may further contain an organic polymer in addition to the ethylenically unsaturated polymerizable compound to provide a cured product with improved characteristics. Examples of such an organic polymer include polystyrene, polymethyl methacrylate, methyl methacrylate-ethyl acrylate copolymers, poly(meth)acrylic acid, styrene-(meth)acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonates, polyvinyl butyral, cellulose esters, polyacrylamides, saturated polyesters, phenol resins, phenoxy resins, polyamide-imide resins, polyamic acid resins, and epoxy resins. Preferred of them are polystyrene, (meth)acrylic acid-methyl acrylate copolymers, and epoxy resins.

The amount of the organic polymer, if used, is preferably 10 to 500 parts by mass per 100 parts by mass of the ethylenically unsaturated polymerizable compound.

The photosensitive composition of the invention may furthermore contain a chain transfer agent, a sensitizer, a surfactant, a silane coupling agent, a melamine compound, and so forth.

As the chain transfer agent or the sensitizer, sulfur-containing compounds are generally used, including mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the recited mercapto compounds; iodized alkyl compounds, such as iodoacetic acid, iodopropionic acid, 2-iodoethanol, 2-iodoethanesulfonic acid, and 3-iodopropanesulfonic acid; aliphatic polyfunctional thiol compounds, such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethylolpropane tristhiopropionate, trimethylolpropane tristhioglycolate, pentaerythritol tetrakisthiopropionate, pentaerythritol tetrakisthioglycolate, trishydroxyethyl tristhiopropionate, diethylthioxanthone, diisopropylthioxanthone, compound C1 shown below, and trimercaptopropionic acid tris(2-hydroxyethyl)isocyanurate; KARENZ MT BD1, PE1 and NR1 available from Showa Denko.

[Chem.18]
Compound C1:

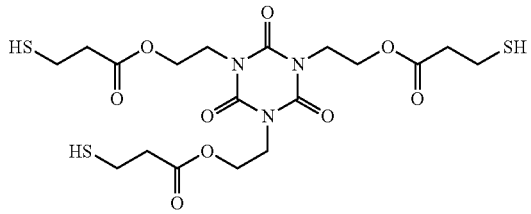 [SMILES: O=C(CCS)OCCn1c(=O)n(CCOC(=O)CCS)c(=O)n(CCOC(=O)CCS)c1=O]

Examples of useful surfactants include fluorine surfactants, such as perfluoroalkyl phosphate esters and perfluoroalkyl carboxylates; anionic surfactants, such as higher fatty acid alkali salts, alkyl sulfonates, and alkyl sulfates; cationic surfactants, such as higher amine halogenates and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants; and silicone surfactants. These surfactants may be used in combination.

Examples of useful silane coupling agents include those manufactured by Shin-Etsu Chemical Co., Ltd. Preferred among them are those having an isocyanate group, a methacryloyl group or an epoxy group, such as KBE-9007, KBM-502, and KBE-403.

Examples of useful melamine compounds include alkyl ether compounds obtained by alkyl-etherifying a nitrogen-containing compounds having active methylol groups ($CH_2OH$) (e.g., (poly)methylolmelamine, (poly)methylolglycoluril, (poly)methylolbenzoguanamine, and (poly)methylolurea) on all or a part (at least two) of their active methylol groups. Examples of alkyl groups constituting the alkyl ether include methyl, ethyl, and butyl, and all of the alkyl groups may be same or may be different. The remaining methylol group(s), if any, that are not alkyl-etherified may be condensed intramolecularly or may be condensed intermolecularly to form an oligomeric component.

Specific examples of such melamine compounds are hexamethoxymethylmelamine, hexabutoxymethylmelamine, tetramethoxymethylglycoluril, and tetrabutoxymethylglycoluril.

Preferred of them are alkyl-etherified melamine compounds, such as hexamethoxymethylmelamine and hexabutoxymethylmelamine.

The photosensitive composition of the invention can be applied to a supporting substrate, such as soda-lime glass, quartz glass, semiconductor substrates, metals, paper, or plastics, by known means, including spin coating, roll coating, bar coating, die coating, curtain coating, various printing techniques, and dipping. The photosensitive composition may be applied once to a supporting substrate such as film and then transferred onto another substrate. The method for the application is not limited.

The sources of energy rays used to cure the photosensitive composition of the invention include ultrahigh pressure mercury lamps, high pressure mercury lamps, medium pressure mercury lamps, low pressure mercury lamps, mercury vapor arc lamps, xenon arc lamps, carbon arc lamps, metal halide lamps, fluorescent lamps, tungsten lamps, excimer lamps, germicidal lamps, light-emitting diodes, and CRT light sources. Electromagnetic energy rays of wavelengths of 2000 to 7000 Å emitted from these light sources and high-energy rays, such as electron beams, X rays, and radial rays are useful. Preferred light sources are ultrahigh pressure mercury lamps, mercury vapor arc lamps, carbon arc lamps, and xenon arc lamps that emit light of 300 to 450 nm.

A laser direct imaging technology is beneficial in the interests of productivity, resolution, and pattern position accuracy, in which a laser beam as an exposure light source is directed to the photosensitive composition without using a mask to directly write an image based on digital information, e.g., from a computer. A laser beam having a wavelength of 340 to 430 nm is suitably used. Lasers emitting light of from the visible to infrared region are also usable, such as excimer lasers, nitrogen lasers, argon ion lasers, helium-cadmium lasers, helium-neon lasers, krypton ion lasers, various semiconductor lasers, and YAG lasers. When these lasers are used, a sensitizing dye that absorbs corresponding light of the visible to infrared region is added.

The photosensitive resin composition of the invention can be used for various applications without particular limitation. It finds use in, for example, photocuring paints or varnishes; photocuring adhesives; printed boards; color filters for liquid crystal display elements of color displays, such as TV monitors, PC monitors, personal digital assistances, and digital cameras; color filters for CCD image sensors; electrode materials for plasma display panels; powder coatings; printing inks; printing plates; adhesives; compositions for dental use; gel coats; photoresists for electronics; electroplating resists; etching resists; dry films; soldering resists; resists used in the manufacture of color filters of various displays or in the formation of structures of plasma display panels, electroluminescent displays, and LCDs; encapsulating compositions for electric/electronic components; solder resists; magnetic recording materials; fine machine parts; waveguides; optical switches; plating masks; etching masks; color test systems; glass fiber cable coatings; screen printing stencils; materials for making a three-dimensional object by stereolithography; holographic recording materials; image recording materials; fine electronic circuits; decolorizing materials; decolorizing materials for image recording materials; decolorizing materials for image recording materials using microcapsules; photoresist materials for printed wiring boards; photoresist materials for direct imaging using UV and visible lasers; and photoresist materials or protective layers used to form dielectric layers in the fabrication of multilayered printed circuit boards.

The photosensitive composition of the invention is also useful in the formation of spacers for LCD panels and the formation of protrusions for vertical-alignment LCD elements. The photosensitive composition is particularly useful for simultaneously forming spacers and protrusions for vertical-alignment LCD elements.

The spacers for LCD panels are preferably produced through the steps of (1) forming a coating film of the photosensitive composition of the invention on a substrate, (2) irradiating the film with radiation through a mask having a predetermined pattern, (3) baking the exposed film, (4) developing the exposed film, and (5) heating the developed film.

When the (colored) photosensitive composition of the invention contains an ink repellent agent, it is suitable as a resin composition for forming barrier ribs in inkjet printing. Such a composition can be used for color filters, particularly preferably used for forming barrier ribs with a profile angle of 50° or greater of inkjet-printed color filters. For that use, a fluorine surfactant or a composition containing a fluorine surfactant is suitably added as the ink repellent agent.

Barrier ribs formed of the photosensitive composition of the invention are transferred to a substrate, and thus the barrier ribs partition a substrate. An optical element is produced by filling the recessed portions surrounded by the barrier ribs with droplets by an inkjet method to form image areas. The droplets preferably contain a colorant so that the image areas may be colored. In that case, the optical element produced by the process described preferably has, on the substrate, at least an array of pixels formed of a plurality of colored areas and barrier ribs separating the colored areas from one another.

The photosensitive composition of the invention can also be used as a composition for forming a protective film or an insulating film. For that use, the composition may contain an ultraviolet absorber, an alkylated melamine and/or an acrylated melamine, and a mono- or bifunctional (meth)acrylate monomer containing an alcoholic hydroxyl group in its molecule and/or silica sol.

The photosensitive composition for a protective film or an insulating film is preferably a resin composition containing, as main components, (A) a carboxyl-containing resin obtained by the reaction between a diol compound and a polycarboxylic acid and having a weight average molecular weight of 2,000 to 40,000 and an acid value of 50 to 200 mgKOH/g, (B) a photopolymerizable unsaturated compound having at least one ethylenically unsaturated bond per molecule, (C) an epoxy compound, and (D) a photopolymerization initiator, the components (C) and (D) being present in amounts of 10 to 40 parts by weight and 0.01 to 2.0 parts by weight, respectively, both per 100 parts by weight of the sum of the components (A) and (B), and the compound represented by formula (I) being contained as the photopolymerization initiator of the component (D).

The insulating film is used as an insulating resin layer formed on a release support to provide a laminate. The laminate is preferably developable with an aqueous alkali solution, and the insulating resin layer preferably has a thickness of 10 to 100 µm.

When the photosensitive composition of the invention contains an inorganic material (inorganic compound), it may be used as a photosensitive paste composition. The photosensitive paste composition may be used for forming baked patterns, such as barrier rib patterns, dielectric patterns, electrode patterns, and black matrix patterns of plasma display panels.

EXAMPLES

The invention will now be illustrated in greater detail with reference to Examples and Comparative Examples, but it should be understood that the invention is not deemed to be limited thereto.

Examples 1-1 to 1-8

Preparation of Compound Nos. 1, 3, 5, 42, 71, 73, 77, and 131

Step 1:

One point zero equivalent of a ketone compound 1(or a ketone compound 1'), 1.2 equivalents of an alkyl halide or an aryl halide, 3.0 equivalents of potassium carbonate, and five times the theoretical amount of dimethyl sulfoxide were mixed and stirred while heating in a nitrogen atmosphere at 130° C. for 3 hours. After cooling the reaction mixture to room temperature, ion-exchanged water was added, and the thus precipitated solid was collected by filtration, which was thoroughly washed and dried to give a ketone compound 2 (or a ketone compound 2').
Step 2:

Preparation of Compound Nos. 1, 3, 5, and 42

One point zero equivalent of the ketone compound 2 obtained in step 1, 1.5 equivalents of hydroxylamine hydrochloride, and double the theoretical amount of dimethylformamide were mixed and stirred while heating in a nitrogen atmosphere at 80° C. for 1 hour. After cooling to room temperature, the reaction mixture was poured into ion-exchanged water for oil-water separation, followed by solvent removal to give an oxime compound 3.

Preparation of Compound Nos. 71, 73, 77, and 131

One point zero equivalent of the ketone compound 2' obtained in step 1 and three times the theoretical amount of dimethylformamide were mixed, and 1.0 equivalent of 35% hydrochloric acid and 1.5 equivalents of isobutyl nitrite were added thereto dropwise while stirring in a nitrogen atmosphere at 5° C. After the addition, the mixture was further stirred at room temperature for 30 hours. Ethyl acetate and water were added to the reaction system for oil-water separation. The organic layer was washed with water and freed of the solvent to give an oxime compound 3'.
Step 3:

One point zero equivalent of the oxime compound 3 (or the oxime compound 3') obtained in step 2 and five times the theoretical amount of dimethylformamide were mixed, and 1.2 equivalents of acetic anhydride was added thereto dropwise while stirring in a nitrogen atmosphere. After the addition, the mixture was further stirred at room temperature for 3 hours. The thus formed precipitate was collected by filtration, thoroughly washed, and dried to yield an oxime ester compound. The results of analyses on the resulting oxime ester compounds are shown in Tables 1 through 3.

TABLE 1

| | Oxime ester compound | Melting point (° C.) | Decomposition point (° C.) |
| --- | --- | --- | --- |
| Example 1-1 | Compound No. 1 | 163 | 191 |
| Example 1-2 | Compound No. 3 | 97 | 219 |
| Example 1-3 | Compound No. 5 | 218 | 254 |
| Example 1-4 | Compound No. 42 | 217 | 235 |
| Example 1-5 | Compound No. 71 | 107 | 174 |
| Example 1-6 | Compound No. 73 | 84 | 174 |
| Example 1-7 | Compound No. 77 | 146 | 159 |
| Example 1-8 | Compound No. 131 | None | 205 |

TABLE 2

| | Chemical shift/ppm (Multiplicity, Proton number) |
| --- | --- |
| Compound No. 1 (DMSO-$d_6$) | 8.20 (d, 1H), 8.02 (s, 1H), 7.49 (s, 1H), 7.25 (t, 1H), 7.17 (t, 1H), 3.85 (s, 3H), 2.34 (s, 3H), 2.23 (s, 3H) |
| Compound No. 3 (CDCl$_3$) | 8.44 (d, 1H), 7.64 (s, 1H), 7.53-7.47 (m, 5H), 7.42 (t, 1H), 7.31 (t, 2H), 2.44 (s, 3H), 2.34 (s, 3H) |
| Compound No. 5 (DMSO-$d_6$) | 8. 54 (s, 1H), 8.49 (d, 2H), 8.41 (d, 1H), 8.03 (d, 2H), 7.77 (d, 1H), 7.41-7.35 (m, 2H), 2.49 (s, 3H), 2.30 (s, 3H) |

TABLE 2-continued

| | Chemical shift/ppm (Multiplicity, Proton number) |
| --- | --- |
| Compound No. 42 (DMSO-$d_6$) | 8.55 (s, 1H), 8.23 (s, 1H), 7.71 (d, 1H), 7.62 (d, 1H), 3.87 (s, 3H), 2.35 (s, 3H), 2.23 (s, 3H) |
| Compound No. 71 (DMSO-$d_6$) | 8.77 (s, 1H), 8.47 (d, 2H), 8.36 (dd, 1H), 7.98 (d, 2H), 7.68 (dd, 1H), 7.43 (t, 1H), 7.41 (t, 1H), 2.73 (t, 2H), 2.26 (s, 3H), 1.55 (m, 2H), 1.27 (m, 6H), 0.83 (t, 3H) |
| Compound No. 73 (DMSO-$d_6$) | 8.75 (s, 1H), 8.37 (dd, 1H), 7.98 (d, 2H), 7.86 (d, 2H), 7.81 (d, 2H), 7.70 (dd, 2H), 7.60 (t, 2H), 7.42 (t, 1H), 7.40 (t, 1H), 2.49 (t, 2H), 2.25 (s, 3H), 1.55 (m, 2H), 1.25 (m, 6H), 0.82 (t, 3H) |
| Compound No. 77 (DMSO-$d_6$) | 8.87 (s, 1H), 8.49 (d, 2H), 8.40 (dd, 1H), 8.07 (d, 2H), 8.01 (d, 2H), 7.73 (m, 2H), 7.61 (t, 2H), 7.45 (t, 1H), 7.43 (t, 1H), 2.89 (t, 2H), 1.64 (t, 2H), 1.39 (t, 2H), 1.25 (m, 4H), 0.79 (t, 3H) |
| Compound No. 131 (DMSO-$d_6$) | 9.00 (s, 1H), 8.50 (d, 2H), 8.31 (dd, 1H), 8.05 (d, 2H), 7.73 (dd, 1H), 7.38 (m , 6H), 2.25 (s, 3H), 2.15 (s, 3H) |

TABLE 3

| | IR absorption spectrum/cm$^{-1}$ |
| --- | --- |
| Compound No. 1 | 1756, 1588, 1539, 1473, 1427, 1366, 1337, 1281, 1208, 1178, 1130, 1107, 1064, 1000, 957, 935, 883, 862, 767 |
| Compound No. 3 | 1752, 1593, 1548, 1499, 1478, 1454, 1360, 1277, 1212, 1189, 1142, 1016, 997, 975, 939, 916, 882, 816, 774 |
| Compound No. 5 | 1769, 1590, 1552, 1500, 1454, 1342, 1322, 1288, 1268, 1217, 1195, 1148, 1105, 976, 935, 916, 864, 846, 810, 748, 735 |
| Compound No. 42 | 2218, 1756, 1594, 1568, 1543, 1482, 1428, 1371, 1238, 1219, 1197, 1150, 1129, 1111, 1008, 1047, 963, 942, 922, 907, 899, 865, 848, 801, 777 |
| Compound No. 71 | 3116, 2927, 2858, 1767, 1631, 1595, 1519, 1502, 1481, 1453, 1345, 1217, 1176, 1101, 1065, 991, 922, 888, 850, 817, 781, 739, 691 |
| Compound No. 73 | 3104, 3053, 2952, 2921, 2852, 1769, 1652, 1628, 1596, 1578, 1516, 1479, 1453, 1446, 1421, 1391, 1362, 1319, 1308, 1278, 1218, 1178, 1153, 1099, 1055, 993, 950, 925, 901, 855, 827, 786, 769, 748, 695 |
| Compound No. 77 | 3122, 3078, 3051, 2951, 2919, 2855, 1749, 1637, 1592, 1500, 1479, 1451, 1390, 1342, 1327, 1313, 1226, 1217, 1176, 1145, 1110, 1074, 1039, 1019, 951, 925, 881, 863, 850, 777, 769, 744, 696 |
| Compound No. 131 | 3120, 3073, 2926, 1766, 1634, 1596, 1524, 1501, 1482, 1454, 1425, 1345, 1314, 1283, 1223, 1173, 1109, 1043, 996, 945, 887, 847, 823, 788, 733, 690, 668 |

Examples 2-1 to 2-4

Preparation of alkali-developable photosensitive resin composition Nos. 1 through 4

Step 1: Preparation of alkali-developable resin

In a reaction vessel were put 100 g of a bisphenol fluorene epoxy resin (epoxy equivalent: 231), which is an epoxy compound represented by general formula (III), 31 g of acrylic acid, 0.26 g of 2,6-di-tert-butyl-p-cresol, 0.11 g of tetra-n-butylammonium bromide, and 33 g of propylene glycol 1-monomethyl ether 2-acetate and stirred at 120° C. for 16 hours. After cooling the reaction mixture to room temperature, 42 g of propylene glycol 1-monomethyl ether 2-acetate, 33 g of biphthalic anhydride, and 0.24 g of tetra-n-butylammonium bromide were added thereto, followed by stirring at 120° C. for 4 hours. To the reaction mixture was further added 10 g of tetrahydrophthalic anhydride, followed by stirring at 120° C. for 4 hours, at 100° C. for 3 hours, at 80° C. for 4 hours, at 60° C. for 6 hours, and finally at 40° C. for 11 hours. To the reaction mixture was then added 138 g of propylene glycol 1-monomethyl ether 2-acetate to give a propylene glycol 1-monomethyl ether 2-acetate solution of a desired alkali-developable resin (Mw=5000; Mn=2100; acid value (of solid content): 92.7 mgKOH/g; solid content: 35 mass %).

Step 2: Preparation of alkali-developable photosensitive resin composition Nos. 1 to 4

The alkali-developable resin (22.0 g) obtained in step 1, 4.3 g of dipentaerythritol penta- and hexaacrylate (Aronix M-402, from Toa Gosei Co., Ltd.), 1.8 g of a 1% cyclohexanone solution of a surfactant (FZ-2122 from Nippon Unicar Co., Ltd.), 5.0 g of propylene glycol 1-monomethyl ether 2-acetate, and 16 g of cyclohexanone were mixed, and 0.1 g of compound No. 5 obtained in Example 1-3, compound No. 71 obtained in Example 1-5, compound No. 73 obtained in in Example 1-6, or compound No. 131 obtained in Example 1-8 was added thereto, followed by thorough stirring to provide alkali-developable photosensitive resin composition Nos. 1 to 4, respectively, which are photosensitive compositions according to the invention.

Comparative Example 1

Preparation of Comparative Alkali-developable Photosensitive Resin Composition No. 1

Comparative alkali-developable photosensitive resin composition No. 1 was prepared in the same manner as in Example 2-1, except for replacing compound No. 5 obtained in Example 1-3 with a commercially available photopolymerization initiator OXE-02 (from BASF).

Evaluation Examples 1-1 to 1-4 and Comparative Evaluation Example 1-1

Evaluation of line Width Sensitivity

Alkali-developable photosensitive resin composition Nos. 1 through 4 and comparative alkali-developable photosensitive resin composition No. 1 were evaluated for sensitivity as follows.

Each composition was applied to a glass substrate by spin coating at 900 rpm for 10 seconds and prebaked on a hot plate at 70° C. for 20 minutes. The prebaked coating film was exposed to light from a high pressure mercury lamp through a pattern mask. The exposed film was developed on a spin development apparatus using a 2.5 mass % aqueous solution of sodium carbonate as a developer for 40 seconds and thoroughly washed with water. The developed film was post-baked in an oven at 230° C. for 60 minutes to fix the pattern. The amount of exposure required to provide a line width of 20 µm through a mask opening width of 20 µm was taken as a line width sensitivity. The results obtained are shown in Table 4.

TABLE 4

| Evaluation example No. | Oxime ester compound used | Alkali-developable photosensitive resin composition No. | Amount of exposure (mJ/cm²) |
|---|---|---|---|
| 1-1 | No. 5 | No. 1 (Example 2-1) | 20 |
| 1-2 | No. 71 | No. 2 (Example 2-2) | 10 |
| 1-3 | No. 73 | No. 3 (Example 2-3) | 20 |
| 1-4 | No. 131 | No. 4 (Example 2-4) | 10 |

TABLE 4-continued

| Evaluation example No. | Oxime ester compound used | Alkali-developable photosensitive resin composition No. | Amount of exposure (mJ/cm²) |
|---|---|---|---|
| Comparative 1-1 | OXE-02 | Comparative No. 1 (Comparative Example 2) | 40 |

It is apparent from Table 4 that the oxime ester compounds of the invention need smaller amounts of exposure, namely exhibit higher line width sensitivity than the compound used in Comparative Example 1.

The oxime ester compound of the invention thus proves excellent in photolithographic performance and therefore useful as a photopolymerization initiator.

The invention claimed is:

1. An oxime ester compound represented by general formula (I):

[Chem. 1]

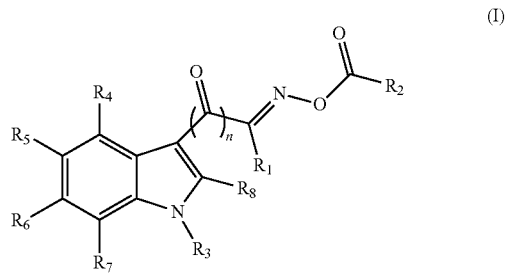

wherein $R^1$ and $R^2$ each independently represent $R^{11}$, $OR^{11}$, $COR^{11}$, $SR^{11}$, $CONR^{12}R^{13}$, or CN;

$R^{11}$, $R^{12}$, and $R^{13}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the alkyl group, the aryl group, the arylalkyl group or the heterocyclic group represented by $R^{11}$, $R^{12}$, and $R^{13}$ being optionally further substituted by $R^{21}$, $OR^{21}$ $COR^{21}$, $SR^{21}$, $NR^{22}R^{23}$, $CONR^{22}R^{23}$, —$NR^{22}$—$OR^{23}$, —$NCOR^{22}$—$OCOR^{23}$, $NR^{22}COR^{21}$, $OCOR^{21}$, $COOR^{21}$, $SCOR^{21}$, $OCSR^{21}$, $COSR^{21}$, $CSOR^{21}$, a hydroxyl group, a nitro group, CN, a halogen atom, or $COOR^{21}$;

$R^{21}$, $R^{22}$, and $R^{23}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the alkyl group, the aryl group, the arylalkyl group or the heterocyclic group represented by $R^{21}$, $R^{22}$, and $R^{23}$ being optionally further substituted by a hydroxyl group, a nitro group, CN, a halogen atom, a hydroxyl group, or a carboxyl group, the alkyl group, the aryl group, the arylalkyl group or the heterocyclic group represented by $R^{11}$, $R^{12}$, $R^{13}$, $R^{21}$, $R^{22}$ and $R^{23}$ having an alkylene moiety optionally interrupted by —O—, —S—, —COO—, —OCO—, —$NR^{24}$—, —$NR^{24}CO$—, —$NR^{24}COO$—, —$OCONR^{24}$—, —SCO—, —COS—, —OCS—, or —CSO— at 1 to 5 sites provided that no two oxygen atoms are directly bonded to each other;

$R^{24}$ represents a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the alkyl group, the aryl group, the arylalkyl group or the heterocyclic group represented by $R^{11}$, $R^{12}$, $R^{13}$, $R^{21}$, $R^{22}$, $R^{23}$, and $R^{24}$ having an alkyl moiety that is optionally branched or cyclic;

$R^3$ represents a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, the alkyl group, the aryl group, the arylalkyl group or the heterocyclic group represented by $R^3$ having an alkyl moiety that is optionally branched or cyclic, $R^3$ and $R^7$, $R^3$ and $R^8$, $R^4$ and $R^5$, $R^5$ and $R^6$, and $R^6$ and $R^7$ being optionally taken together to form a ring, the alkyl group, the aryl group, the arylalkyl group or the heterocyclic group represented by $R^3$ being optionally further substituted by $R^{21}$, $OR^{21}$, $COR^{21}$, $SR^{21}$, $NR^{22}R^{23}$, $CONR^{23}R^{23}$, $-NR^{22}-OR^{23}$, $-NCOR^{22}-OCOR^{23}$, $NR^{22}COR^{21}$, $OCOR^{21}$, $COOR^{21}$, $SCOR^{21}$, $OCSR^{21}$, $COSR^{21}$, $CSOR^{21}$, a hydroxyl group, a nitro group, CN, a halogen atom, or $COOR^{21}$;

$R^4$, $R^5$, $R^6$, and $R^7$ each independently represent $R^{11}$, $OR^{11}$, $SR^{11}$, $COR^{14}$, $CONR^{15}R^{16}$, $NR^{12}COR^{11}$, $OCOR^{11}$, $COOR^{14}$, $SCOR^{11}$, $OCSR^{11}$, $COSR^{14}$, $CSOR^{11}$, a hydroxyl group, CN, or a halogen atom, $R^4$ and $R^5$, $R^5$ and $R^6$, and $R^6$ and $R^7$ being optionally taken together to form a ring;

$R^{14}$, $R^{15}$, and $R^{16}$ each represent a hydrogen atom or an alkyl group having 1 to 20 carbon atoms, the alkyl group represented by $R^{14}$, $R^{15}$, and $R^{16}$ being optionally branched or cyclic;

$R^8$ represents $R^{11}$, $OR^{11}$, $SR^{11}$, $COR^{11}$, $CONR^{12}R^{13}$, $NR^{12}COR^{11}$, $OCOR^{11}$, $COOR^{11}$, $SCOR^{11}$, $OCSR^{11}$, $COSR^{11}$, $CSOR^{11}$, a hydroxyl group, CN, or a halogen atom; and n represents 0 or 1, and the oxime ester compound represented by general formula (I) satisfies any of following (1) to (4):

(1) n is 1, (2) at least one of $R^4$, $R^5$, $R^6$, and $R^7$ is $R^{11}$, $OR^{11}$, $SR^{11}$, $COR^{14}$, $CONR^{15}R^{16}$, $NR^{12}COR^{11}$, $OCOR^{11}$, $SCOR^{11}$, $OCSR^{11}$, $COSR^{14}$, $CSOR^{11}$, a hydroxyl group, CN, or a halogen atom; and satisfies the following conditions (2-1) and (2-2);

(2-1) when any of $R^4$, $R^5$, $R^6$, and $R^7$ is $R^{11}$, $R^{11}$ represents an alkyl group having 1 to 20 carbon atoms, an aryl group having 6 to 30 carbon atoms, an arylalkyl group having 7 to 30 carbon atoms, or a heterocyclic group having 2 to 20 carbon atoms, and the hydrogen atom of the group represented by $R^{11}$ is further substituted by $OR^{21}$, $COR^{21}$, $SR^{21}$, $NR^{22}R^{23}$, $CONR^{22}R^{23}$, $-NR^{22}-OR^{23}$, $-NCOR^{22}-OCOR^{23}$, $NR^{22}COR^{21}$, $OCOR^{21}$, $COOR^{21}$, $SCOR^{21}$, $OCSR^{21}$, $COSR^{21}$, $CSOR^{21}$, a hydroxyl group, a nitro group, CN, a halogen atom, or $COOR^{21}$;

(2-2) when any of $R^4$, $R^5$, $R^6$, and $R^7$ is $OR^{11}$, $OR^{11}$ represents an alkyl group having 1 to 20 carbon atoms, an aryl group having 6 to 30 carbon atoms, an arylalkyl group having 7 to 30 carbon atoms, or a heterocyclic group having 2 to 20 carbon atoms, and the hydrogen atom of the group represented by $R^{11}$ is further substituted by $OR^{21}$, $COR^{21}$, $SR^{21}$, $NR^{22}R^{23}$, $CONR^{22}R^{23}$, $-NR^{22}-OR^{23}$, $-NCOR^{22}-OCOR^{23}$, $NR^{22}COR^{21}$, $OCOR^{21}$, $COOR^{21}$, $SCOR^{21}$, $OCSR^{21}$, $COSR^{21}$, $CSOR^{21}$, a hydroxyl group, a nitro group, CN, a halogen atom, or $COOR^{21}$;

(3) $R^3$ is an arylalkyl group having 7 to 30 carbon atoms or a heterocyclic group having 2 to 20 carbon atoms, (4) $R^3$ and $R^7$, $R^3$ and $R^8$, $R^4$ and $R^5$, $R^5$ and $R^6$, or $R^6$ and $R^7$ are taken together to form a ring.

2. The oxime ester compound according to claim 1, being represented by general formula (II):

[Chem. 2]

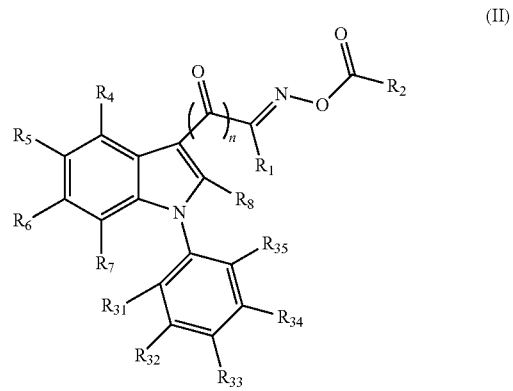

(II)

wherein $R^1$, $R^2$, $R^4$, $R^5$, $R^6$, $R^7$, $R^8$, and n are as defined for general formula (I); $R^{31}$, $R^{32}$, $R^{33}$, $R^{34}$, and $R^{35}$ each independently represent $R^{11}$, $OR^{11}$, $SR^{11}$, $COR^{11}$, $CONR^{15}R^{16}$, $NR^{12}COR^{11}$, $OCOR^{11}$, $COOR^{14}$, $SCOR^{11}$, $OCSR^{11}$, $COSR^{14}$, $CSOR^{11}$, a hydroxyl group, a nitro group, CN, or a halogen atom; $R^{31}$ and $R^{32}$, $R^{32}$ and $R^{33}$, $R^{33}$ and $R^{34}$, and $R^{34}$ and $R^{35}$ may be taken together to form a ring.

3. A photopolymerization initiator comprising the oxime ester compound according to claim 2.

4. The oxime ester compound according to claim 2, wherein $R^{31}$, $R^{32}$, $R^{33}$, $R^{34}$, or $R^{35}$ is a nitro group, CN, a halogen atom or $COR^{11}$, and $R^{11}$ is an aryl group having 6 to 12 carbon atoms or an alkyl group having 1 to 8 carbon atoms.

5. The oxime ester compound according to claim 4, wherein $R^{31}$, $R^{32}$, $R^{33}$, $R^{34}$, or $R^{35}$ is a nitro group or $COR^{11}$, and $R^{11}$ is an aryl group having 6 to 12 carbon atoms.

6. The oxime ester compound according to claim 5, wherein at least one of $R^4$, $R^5$, $R^6$, and $R^7$ is CN.

7. A photopolymerization initiator comprising the oxime ester compound according to claim 1.

8. A photosensitive composition comprising the photopolymerization initiator according to claim 7 and a polymerizable compound having an ethylenically unsaturated bond.

9. An alkali-developable photosensitive resin composition comprising the photosensitive composition according to claim 8 and a compound having alkali developability and optionally having an ethylenically unsaturated group.

10. A colored alkali-developable photosensitive resin composition comprising the alkali-developable photosensitive resin composition according to claim 9 and a colorant.

11. A cured product obtained by irradiating the colored alkali-developable photosensitive resin composition according to claim 10 with energy rays.

12. A cured product obtained by irradiating the alkali-developable photosensitive resin composition according to claim 9 with energy rays.

13. A cured product obtained by irradiating the photosensitive composition according to claim 8 with energy rays.

14. A method for producing a cured product comprising a step of irradiating the photosensitive composition according to claim 8 with energy rays.

15. The oxime ester compound according to claim 1, wherein at least one of $R^4$, $R^5$, $R^6$, and $R^7$ is the following (11) or (12);

(11) CN,

(12) $OR^{11}$, wherein $R^{11}$ is an alkyl group having 1 to 20 carbon atoms, an aryl group having 6 to 30 carbon atoms, an arylalkyl group having 7 to 30 carbon atoms, or a heterocyclic group having 2 to 20 carbon atoms, and the alkyl group, the aryl group, the arylalkyl group or the heterocyclic group represented by $R^{11}$ is further substituted by $OR^{21}$, $COR^{21}$, $SR^{21}$, $NR^{22}R^{23}$, $CONR^{22}R^{23}$, $-NR^{22}-OR^{23}$, $-NCOR^{22}-OCOR^{23}$, $NR^{22}COR^{21}$, $OCOR^{21}$, $SCOR^{21}$, $OCSR^{21}$, $COSR^{21}$, $CSOR^{21}$, a hydroxyl group, a nitro group, CN, a halogen atom, or $COOR^{21}$.

16. The oxime ester compound according to claim 1, wherein $R^3$ is a heterocyclic group having 2 to 20 carbon atoms.

\* \* \* \* \*